United States Patent [19]

Shah et al.

[11] Patent Number: 4,583,553

[45] Date of Patent: Apr. 22, 1986

[54] AMBULATORY ECG ANALYZER AND RECORDER

[75] Inventors: Atul P. Shah, Palm Bay; James L. Reuss, Melbourne Beach; Toni Guckert, W. Melbourne; Jeffrey J. Clesius, Palm Bay, all of Fla.

[73] Assignee: Medicomp, Inc., Melbourne, Fla.

[21] Appl. No.: 551,829

[22] Filed: Nov. 15, 1983

[51] Int. Cl.$^4$ ............................................. A61B 5/04
[52] U.S. Cl. ................................... 128/704; 128/708
[58] Field of Search ............... 128/695, 696, 702, 703, 128/708

[56] References Cited

U.S. PATENT DOCUMENTS

| | | | |
|---|---|---|---|
| 3,658,055 | 4/1972 | Abe et al. | 128/703 |
| 3,830,228 | 8/1974 | Foner | 128/696 |
| 3,880,147 | 4/1975 | Gruenke et al. | 128/702 |
| 3,903,874 | 9/1975 | Shakespeare | 128/696 |
| 4,023,564 | 5/1977 | Valiquette et al. | 128/708 |
| 4,090,505 | 5/1978 | Mortara | 128/702 |
| 4,112,930 | 9/1978 | Feldman et al. | 128/704 |
| 4,170,227 | 10/1979 | Feldman et al. | 128/704 |
| 4,170,992 | 10/1979 | Dillman | 128/702 |
| 4,193,393 | 3/1980 | Schlager | 128/702 |
| 4,240,442 | 12/1980 | Andresen et al. | 128/708 |
| 4,263,919 | 4/1981 | Levin | 128/708 |

FOREIGN PATENT DOCUMENTS 00419 10/1981 PCT Int'l Appl.

*Primary Examiner*—William E. Kamm
*Attorney, Agent, or Firm*—Barnes & Thornburg

[57] ABSTRACT

An ambulatory cardiac analyzer and recorder includes an allocation and priority scheme which has quotas for classes of QRS events and priority between types of events within a class. The quality of a low priority event is used to replace a similar type of event when the memory is full. The peak detection, QRS identification and classification circuit process and correlate information from both of two input channels. This allows quicker and more accurate determination of QRS waveforms as well as typical QRS waveforms.

20 Claims, 16 Drawing Figures

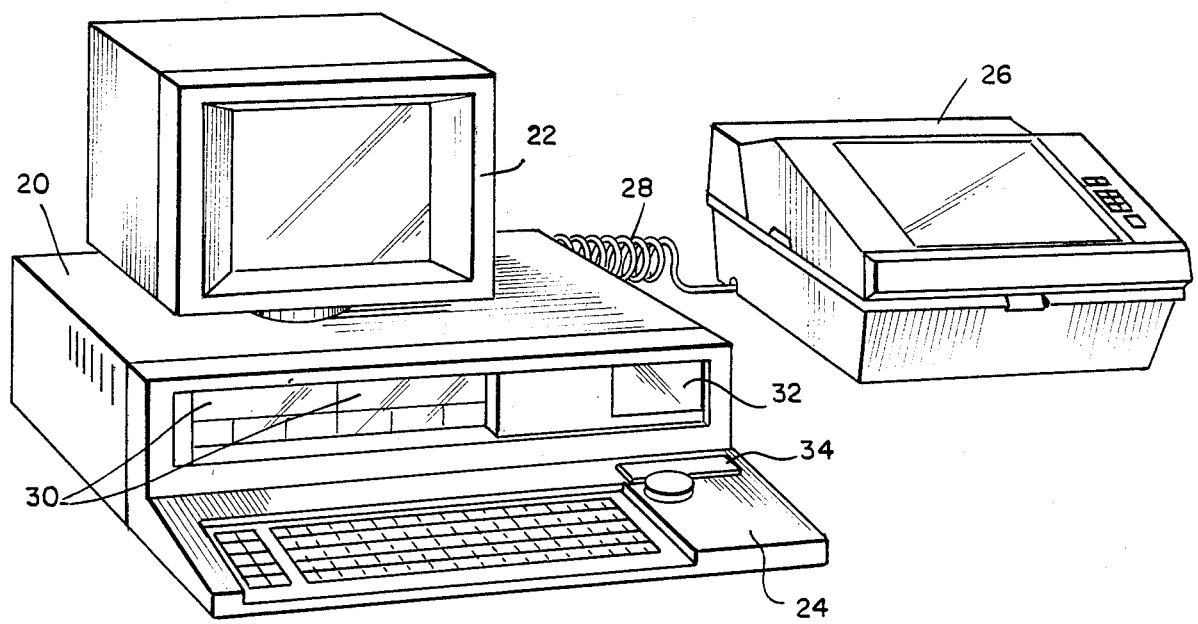
FIG. 1
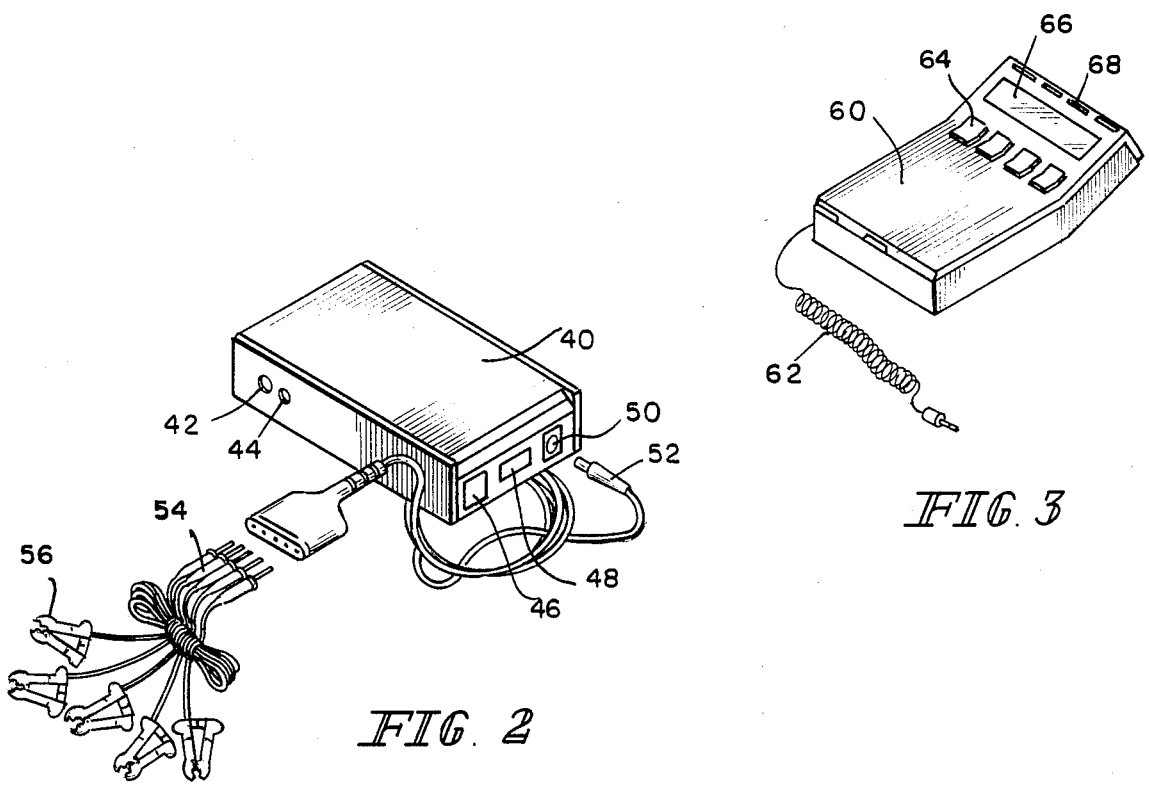
FIG. 2
FIG. 3

AMBULATORY ECG ANALYZER AND RECORDER

BACKGROUND AND SUMMARY OF THE INVENTION

The present invention relates generally to ECG analyzers, and more specifically to ambulatory ECG analyzers and reporters.

It is well recognized that there is a need to monitor the ECG of a patient during a 24 hour period of normal activity versus the setimentary ECG monitoring in an office. To improve the analysis of the patient, real time ECG monitors and recorders, which are capable of being carried on the patient, have been developed To keep the size of the device down, the systems have compromised the ability to make sohpisticated decisions. Generally, the prior art uses a magic formula or algorithm to determine QRS waveforms and to provide some real time analysis. These systems are difficult to implement as well as require substantial fine tuning in order to properly identify QRS waveforms and to extract the needed information as well as classifying the waves for a plurality of atypical events. Similarly, because of limited storage space, only a limited number of ECG data strips could be stored. Crude attempts at prioritizing the data strips to be stored have been used.

An object of the present invention is to provide an ambulatory ECG analyzer and reporting system which provides substantially more real time data than previously available.

Another object of the present invention is to provide an embulatory ECG analyzer and recorder with a more efficient memory priority system.

Still another object of the present invention is to provide an ECG analyzer using a correlation process between two input channels.

A further object of the present invention is to provide an ECG analyzer and reporting system which is capable of monitoring the impedance of the leads before the monitoring period.

A still further object of the present invention is to provide a moving ECG display on an electronic display from digital data.

An even further object of the present invention is to provide an ambulatory ECG analyzer which is capable of detecting and eliminating pacemaker spikes.

A still even further object of the present invention is to provide a memory mapping in the ambulatory unit to increase the addressing capability of the memory beyond that of the standard CPU ability.

Yet another further object of the present invention is to provide a QRS identification and classification scheme based on a heierarchy of decision making processes and including previously determined information.

These and other objects will be apparent from the following detailed description of the drawings.

BRIEF DESCRIPTION OF THE DRAWINGS

FIG. 1 is a perspective view of a base station and printer.

FIG. 2 is a perspective view of a portable ambulatory ECG analyzer and recorder with patient lead set.

FIG. 3 is a perspective view of a ambulatory diary.

DETAILED DESCRIPTION OF THE DRAWINGS

Figure 4:
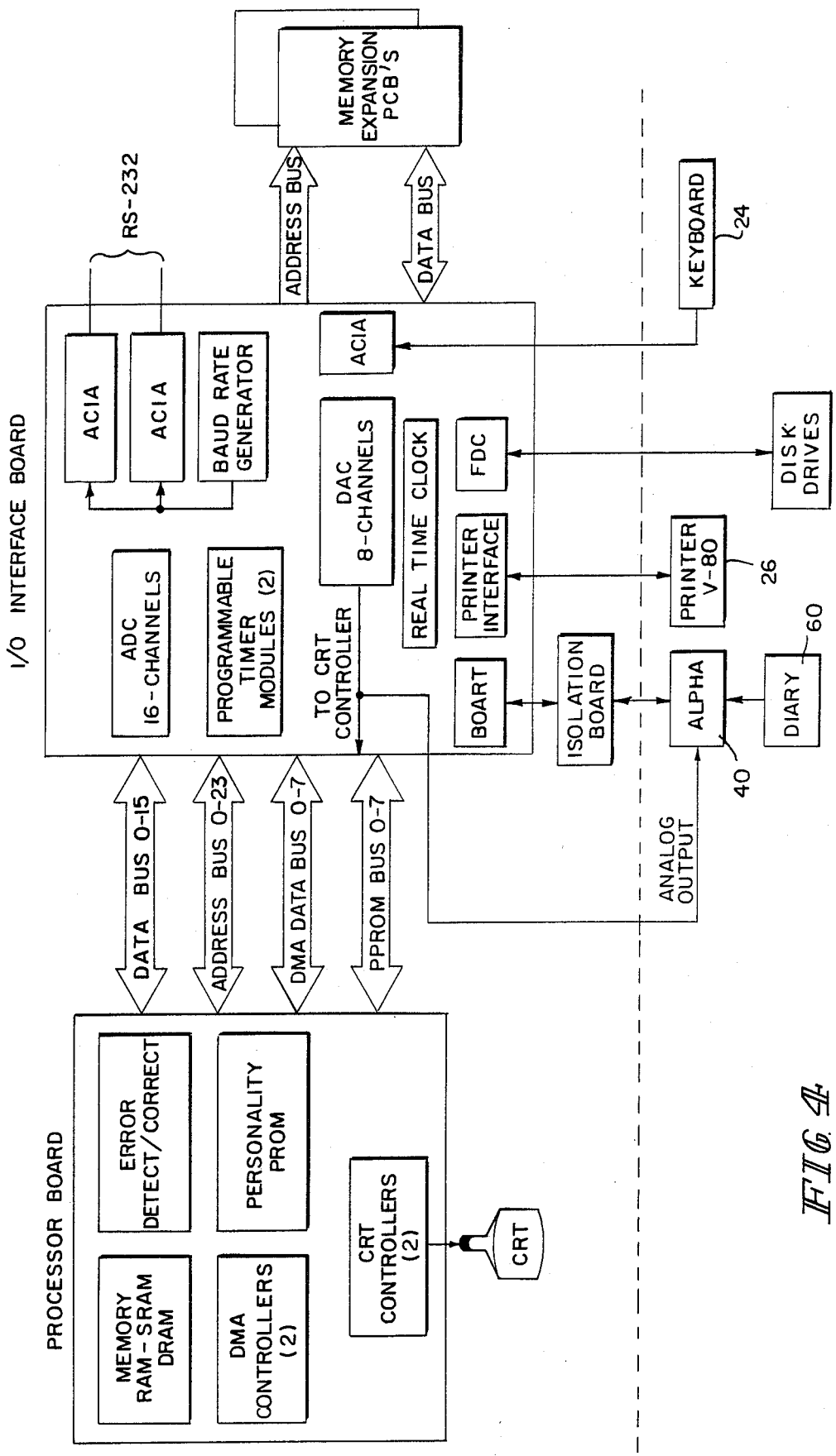
FIG. 4 is a block diagram illustrating the inter-relationships of the base station, printer, ambulatory ECG analyzer, and diary.

The computerized ambulatory ECG analyzer includes a base station as illustrated in FIG. 1 and portable portions as illustrated in FIGS. 2 and 3. The base station includes an Omega unit 20 having a visual display unit 22 thereon, a keyboard 24 and a printer 26 connected to the base unit by cable 28. The Omega or base station 20 includes a pair of disc drives 30, a cable port 32 for the portable unit or Alpha and a tray 34 to receive the Alpha or portable unit. The portable Alpha unit 40 including a battery supply is carried by the patient to be monitored. Port 42 receives a cable to connect the Alpha unit to the base station Omega 20, a port 44 for the electronic diary, a mark button 46, a visual display 48 and a port 50 for patient leads. A cable 52, which is connectable to patent lead port 50, receives five lead wires 54 which are connected to five electrodes 56.

The electronic diary 60 is illustrated in FIG. 3 as including a housing with a cord 62 which is received in port 44 of the Alpha unit 40. The electronic diary 60 includes a plurality of buttons 64, a visual display 56 and sound transmission ports 68.

The base unit or Omega 20 is used to initialize and test the Alpha unit 40 prior to use. The physician has the opportunity to view the operational status of the Alpha and a model QRS waveform as well as modifying variables and ranges to be used as well as the ranges in the Alpha. Subsequent to use, the Omega 20 allows viewing as well as printing of the real time information analyzed and stored by the Alpha unit 40. The Alpha unit 40 provides real time monitoring, analysis and recording of ECG information and is worn by the patient. The electronic diary 60 is also worn by the patient and may be activated by the user or automatically upon detection of events of interest by the Alpha unit 40 to request information from the patient being monitored. As will be explained more fully below, the interrogation may be via the visual display 66 or the audio ports 68.

Figure 5A:
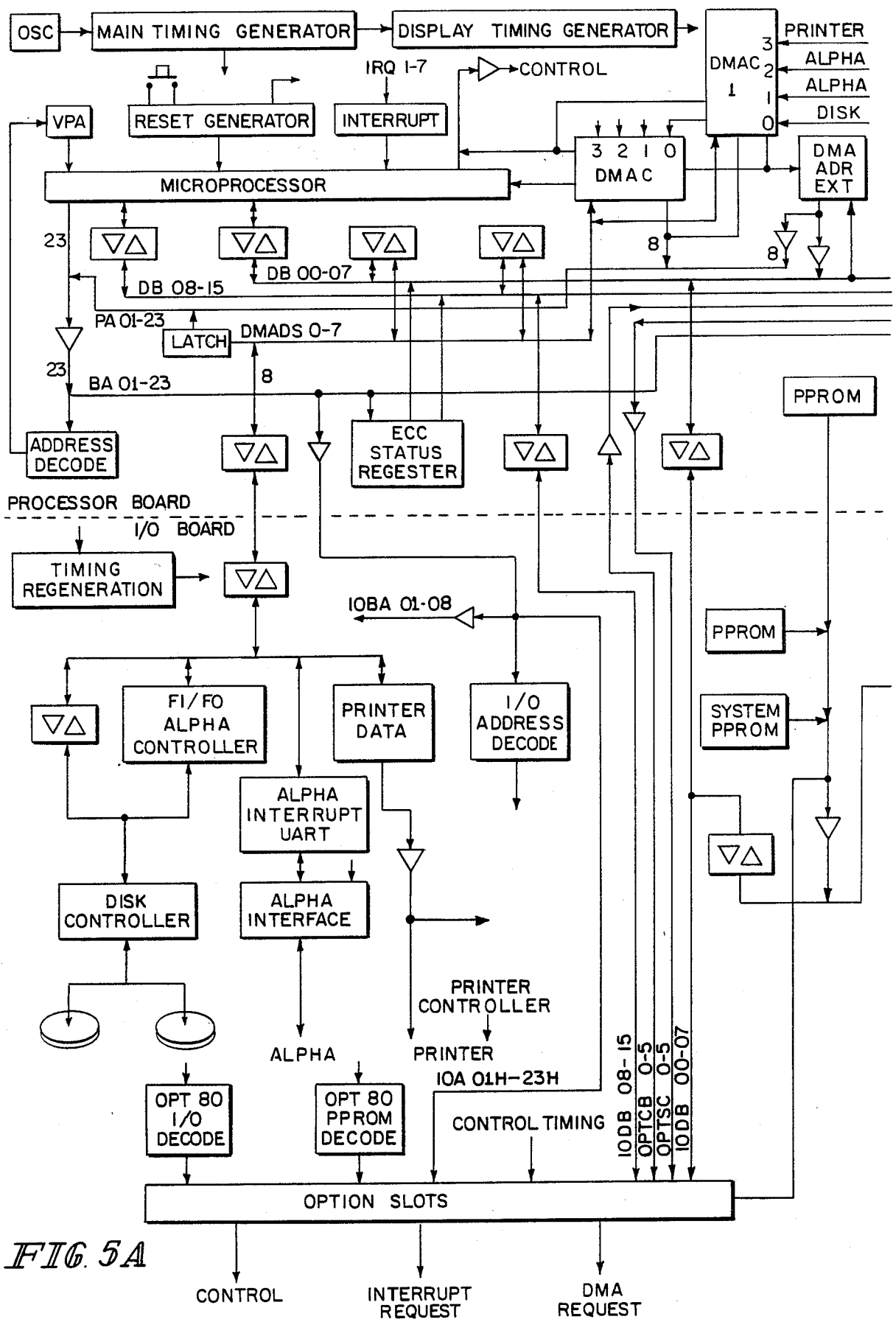
FIGS. 5A and 5B are block diagrams of a bus structure of the base station.
Figure 5B:
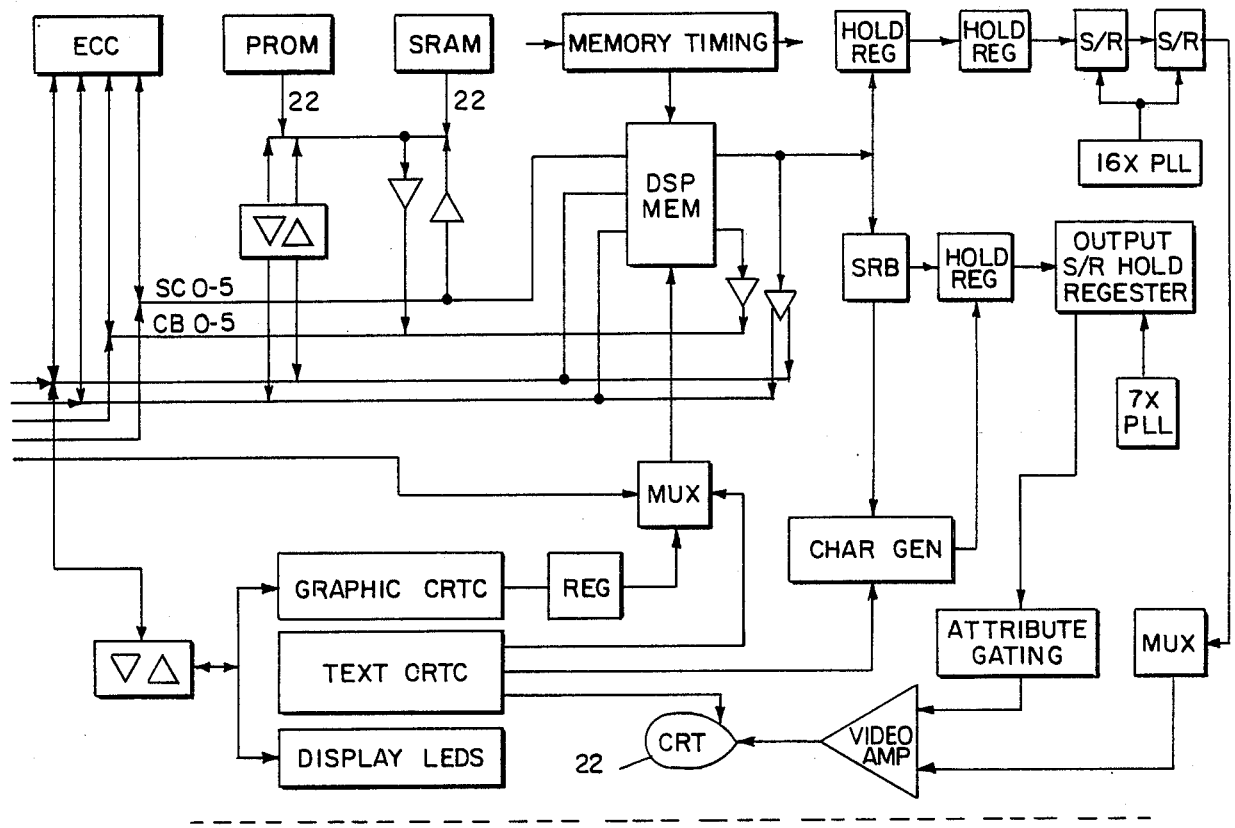
Figure 5B:
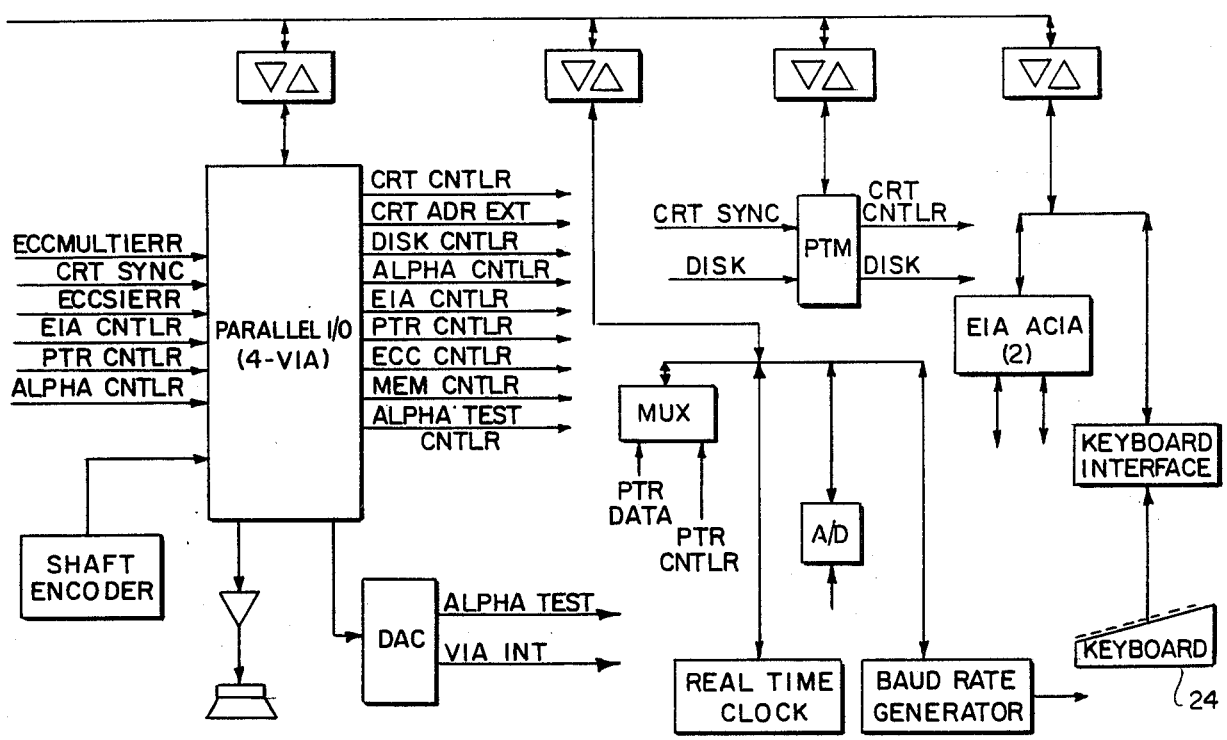

The electronics for the Omega unit 20 are illustrated in FIGS. 4 and 5A and 5B and consist of a microprocessor, memory and controllers for the various subsystems such as the CRT, printer, Alpha interface, floppy disk, serial communication port and support circuitry.

The basic intelligence of the Omega unit 20 is provided by a sixteen bit microprocessor. It controls and directs the various subsystem and information flow through the Omega System. It does this by reading and executing instructions in the memory. It has control and timing signals, address and data paths that it uses to acquire and deposit this information in memory. The various subsystems that it controls are also communicated with in this same way. They appear to be memory cells just as the dynamic RAM, static RAM and PROM are accessed.

The memory is composed of three different types. The dynamic RAM is used on the main program (instructions) and data storage area. It also provides the graphic and text buffers for the CRT subsystem. The dynamic RAM needs to be continually accessed so that it will maintain its content intact. Without this accessing (refreshing) the contents will change and become useless. This refreshing action is provided by the text CRT subsystem logic.

The static RAM is used to hold important program information and for system diagnostic purposes. Because it has no need to be refreshed it is considered to be more reliable in the event of system malfunction.

The PROM contains the necessary instructions and data to initialize the system. The PROM has basic diagnostic routines which verify key portions of the system are operational. It also contains a loader program which reads the main operational software from the floppy disc electronics into the main memory. This bootstrap program and the other contents of the PROM are maintained even if the system loses power. The static and dynamic RAM content are lost when power is removed.

All three types of memory are supported by Error Correction and Detection logic. This logic is capable of detecting errors which may occur if one or two bits are in error. It will correct a single bit failure. This feature is controlled by the microprocessor and may be turned on or off by program control.

The CRT (Cathode Ray Tube) 22 is a raster scan monochrome display unit. It provides information to the operator in a visual format using both text and graphics. Two controllers, one for each text and graphic, are used to provide the control signals, addressing and timing signals necessary to convert the information (bits) in the dynamic RAM to images on the CRT. The microprocessor instructs these controllers as to the specifics of the timing information and memory addresses.

The two formats, namely, text and graphics, are formed separately and merged just before being sent to the CRT 22 itself. The data is read (address, timing and control signals are provided) from the dynamic memory into a circulating buffer. This buffer provides storage for a complete line of text on the screen. This data contained in the buffer, with the number of the scan line in the line of text is used as an address to a character generator PROM. The output of this PROM (8 bits parallel) is then serialized. Each bit which is present (1) caused a light spot to appear on the CRT face. A missing bit (0) causes that position to remain dark. The serialized stream is then fed through logic which may cause the data pattern to exchange 1's for 0's thus causing the light areas and dark areas to be exchanged (reverse video) to blink, by turning off the dots at a predefined rate, or to be displayed in an alternate intensity. Two Digital to Analog (D-A) converters may be programmed by the microprocessor to vary the intensity of the light areas on the screen of the CRT. This is done by varying the voltage of the signal provided to the CRT screen. A facility also exists for providing an underline to each character area which could be displayed on the screen.

The graphic controller has its timing slaved to the text controller. This synchronizes the opeeration of the two units so that the relationship of the text and graphics display on the CRT screen are controlled. The graphics controller can be prevented under program control from reading from memory and displaying on the CRT. This allows other units more frequent access to the memory, increasing the speed of operation of the total system.

The graphics CRT controller emits address and control signals to the dynamic RAM. The RAM then performs a memory read cycle. The sixteen bits of data are then latched. This latched data is then transferred to a latched synchronized to the graphics controller dot clock which represent the frequency that the graphic video information is transferred to the CRT tube. This latched data is transferred to a shift register to convert it to a serial data stream. A multiplexer is then used to select which of the various positions along the shifting data stream is merged with the test video stream. This multiplexer is program controlled. The microprocessor can select which particular position it wants. As it selects earlier taps (positions closer in the data flow to the memory), the image on the screen appears to shift to the left. Thus by selecting succeedingly earlier taps the image on the CRT tube appears to move to the left. A D-A converter is also used to vary the intensity of the graphic video on the screen. This is done by controlling the voltage of the video signal sent to the CRT tube.

A DMA controller is available in the system. It is used to transfer data between memory and a controller. The DMA perform programmed transfers that are instructed by the microprocessor. This also causes data movement without the direct involvement of the microprocessor, freeing it to execute instructions and increasing the total system throughout. The DMA can exchange data between the floppy disc controller and memory, and Printer interface and memory or to and from the Alpha interface and memory. It has additional inputs which may be used by any expansion units for DMA controlled transfers.

The Floppy Disc Controller is capable of handling four floppy disc drives of either the 5¼ or 8 inch variety. The controller is programmed by the microprocessor to find, write or read data from the disc drives. The drives send back serial data which is decoded and turned into parallel data. To write data a serial data steam is sent to the drives. This stream originates as eight byte parallel data sent to the controller. Data transfers to or from the controller may be from the microprocessor directly. The microprocessor may, however, program the DMA to accomplish the transfer. The DMA then transfers data to (or from) a FIFO (First In - First Out memory element) from (or to) the memory. A transfer then takes place between the disc controller and the FIFO. This mechanism smooths the data flow between the controller and memory. Because the data is transferred between the controller and disc at a fixed rate, and the transfer between memory may be slower than this rate for some intervals this buffering mechanism (FIFO) is necessary.

The Alpha Interface allows the microprocessor to transfer data and control the Isolation board. This board provides electrical isolation between the Omega 20 and the Alpha 40. This interface allows the microprocessor to detect the presence of an Alpha 40 to reset the Alpha, to provide power to the ALPHA, and to communicate with the Alpha unit over a duplex serial communication line. All of these signals are electrically isolated from the Alpha by the Isolation Board.

The data transfer between the Alpha Interface and the microprocessor can take place directly or the DMA can be programmed to transfer the data between the interface and memory. Each of the duplex paths (to or from memory) has a separate section of the DMA controller so thay can be individually selected and are not on one another.

The Printer is controlled by the microprocessor using the printer interface. The control of the printer provided by this interface is accomplished by the microprocessor setting and clearing bits in its memory address space. It can send control signals like: Remote Line Terminate, Remote End of Transmission, Remote Form Feed, Remote Reset, Simultaneous Print/Plot, and Clear. Data transfers may be done directly by the microprocessor or the DMA may be programmed to perform them. The ability to read the data presented to the printer exists. This diagnostic allows the microprocessor to fully test the data path to the printer.

Various counter and timer functions are available to the microprocessor. These are used for timing certain critical functions and counting certain events. Head load timing for the disc controller, CRT controller horizontal sync pulses are counted for timing various system function and scheduling events. The number of Alpha data transfers are counted to provide information about when to examine the data.

A DAC (Digital to Analog Converter) has two functions. It provides intensity control for two text intensities and the graphics intensity. It also provides two analog signals to be used to test the Alpha analog input circuit. These test signals are programmed by the microprocessor.

The Real Time clock provides time of day and calendar functions for the base unit. In addition a small amount of RAM is present. Both of these are backed up by a battery. This provides power to these circuits while the main power is off. This allows accurate time keeping and a small amount of storage that will survive while the system is unpowered.

Two RS232 compatible serial interfaces are present in the Omega unit 20. These provide the capability of communicating with the base unit using any RS232 compatible device. They are programmed directly by the microprocessor and all data transfers are accomplished by the microprocessor.

The keyboard information is received in serial format. The interface then makes eight bit parallel data out of this serial stream. The microprocessor then reads this data from the interface.

The knob generator pulses which lead or lag one another depending on the direction the knob is being turned. The interface counts the pulses in two different counters. One counts the pulses generated by turning the knob in a clockwise fashion, the other counter counts pulses generated by turning the counter in a counter-clockwise fashion.

The isolation module provides an interface between the main electronics module and the Alpha 40. A DC to DC converter converts 12 volt power from the power supply to the isolated Alpha side of the supply. This supply electrically isolates the main electronics from the Alpha.

The control and data signals are isolated from the main electronics assembly using optically coupled semiconductor devices. This allows digital signals to be passed from one side to the other without a direct electrical path of any sort. The isolated side can detect the presence of an Alpha 40, and the Alpha drawing an excessive current from the isolated power supply. The main electronics can send signals over the optically coupled interface to reset the Alpha and control the isolated power supply powering the Alpha.

There are other signals used to establish a full duplex serial communication path between the Alpha and the main electronic module.

The base unit contains an assembly upon which floppy disc drives are mounted. These drives accept digital control and data signals which cause the reading or writing of data upon a flexible disc media. This media (an iron oxide coated flexible mylar disc) is used to store and retrieve data. These drives are the necessary mechanical and electrical assemblies to transfer the data from the floppy disc controller on the main electronics module to the flexible media.

A monitor is mounted in a swivel mounted assembly atop the base unit. This monitor employs a CRT and electronics necessary to convert signals to a light emitting pattern on the tube. This digital signals consists of vertical sync, horizontal sync and video data. The two sync signals synchronize the horizontal scanning frequency and the vertical scanning frequency of the CRT electronics to the main electronics module. The video data then modulates the electronics to the main electronics module. The video data then modulates the electronics to cause the desired pattern to appear on the CRT.

Power for the CRT is supplied from the Omega unit 20.

The keyboard contains circuitry which converts a keystroke to a code which is serially sent to the Omega unit. The code defines the particular key which was activated and whether the stroke was an upstroke or a downstroke.

The knob encodes rotary motion into two digital pulse trains. A pulse is produced in relationship to the angular displacement of the knob. One pulse train leads or lags the other depending on the direction of rotation of the knob.

The base unit contains a power supply module to provide a DC power for the base unit assemblies and the keyboard. This supply accepts AC power at 110 volts or 220 volts (nominal) 60 Hertz. It converts this to $+5$ volts and $+12$ volts DC power. Because of the small space available and the weight requirements the conversion techniques used is that used in switching power supplies.

This supply also conforms to the U.L. (Underwriter Laboratories) requirements for patient attached medical equipment.

Figure 6:
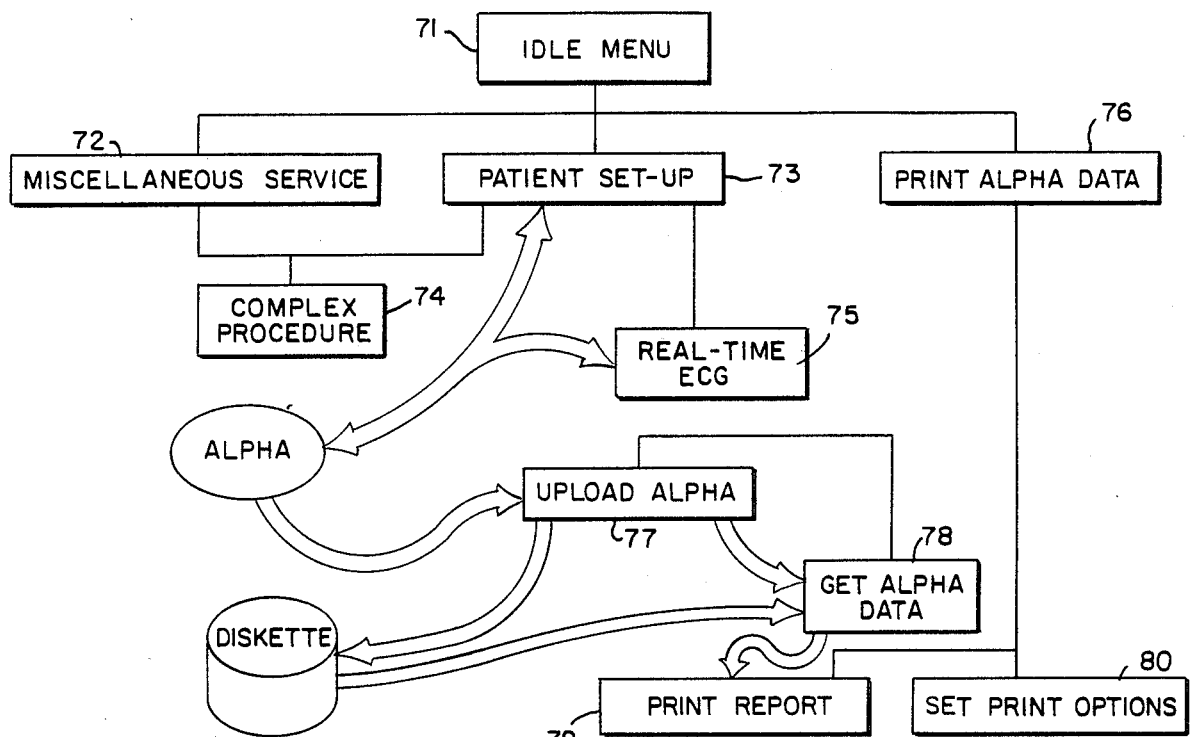
FIG. 6 is a software block diagram for the base station.

Omega Software:

The Omega software as illustrated in FIG. 6 is a menu driven system that is used to initiate patient procedure and print post procedure ports.

OMEGA

The idle menu 71 is displayed on the CRT after the initial system start-up. From here, the user may select one of three basic system functions: (1) Set-up a Patient 73, (2) Print a Report 79, and (3) Miscellaneous Services 72. After chosing and completing one of the possible functins, the system choice once again becomes "idle" and returns to Menu 71.

Menu 72 allows the user to perform functions that are not directly related to a particular patient. Functions at this level include: (a) Definition of Procedure Protocols; (b) Addition and Deletion of Physician Names; (c) Set Date and Time; (d) Change System Password. Definition of procedure protocols allows the user to define "standard" protocols that will be used for most patients. Therefore, the patient may be quickly set-up by selecting one of the predetermined protocols.

The Patent Set-Up 73 option of the idle menu is selected by a technician when running a procedure on a patient. A series of menus are displayed that allow the user to select and/or define the protocol and store patient related information. Patient Information allows the technician to enter the patient's name, address, weight, height, etc. Physician and Protocol Selection menu presents the user with choices of previously entered physician names and protocols from miscellaneous services 72 details. The user may select from the predefined choices or enter a new physician name and protocol definition. Physician names and protocol definitions that are entered during patient set-up are used as "one time" choices and are not made part of the permanent physician and protocol files. Real-Time ECG Display menu allows the user to view the analog data that is being "seen" by the Alpha via the patient cable which is attached to the Alpha. The user now has several options that may be chosen in order to "tailor" the Alpha to the patient. As options are chosen, the results are immediately displayed on the CRT so that the user may see the results of his selections. These options include: (a) gain control, (b) lead impedance, (c) typical QRS, (d) grid on/off and (e) verification menu.

The user may select one of three gains for each channel in order to produce a signal of sufficient amplitude for proper analysis. Lead Impedance allows the user to examine the electrical resistance between the electrodes that have been placed on the patient. If the impedance values are too high, an improper skin preparation is implied and the user may wish to improve the skin preparation. A detailed explanation for lead impedance measuring will be discussed below in reference to the Alpha Hardward and FIG. 11.

Typical QRS commands the Alpha to search for a QRS complex that it will consider a typical. This typical beat is used as a pattern by which all beats will be compared for the duration of the procedure. After the Alpha has made its selection, the beat displayed on the CRT and the user may approve or disapprove. This continues until an acceptable complex is found. As the Alpha views several seconds of data before making its selection, the first complex is chosen is used in most cases. Grid On/Off allows the user to superimpose the ECG trace on a grid scale. The scale can be used for measuring the amplitude of each beat and is useful when attempting to select the proper gain for the particular patient.

Verification Menu presents to the user all options that may have been chosen for the procedure and the patient information. It is intended that the user view this "last chance" data before it is loaded into the Alpha and the procedure started. The user may change any selected option (or select more options) by backing up one or more menus and making the appropriate corrections.

Once the procedure is approved by the user, the protocol and patient information is downloaded into the Alpha, the procedure is started, and the Omega returns to the idle menu.

Complex Procedure 74 are a series of menus which may be entered via miscellaneous services 72 or patient set-up 73. They are used to define the protocols that are used for patient procedures. Heart rate, event priorities and report options may be defined for each protocol. The Alpha is capable of reporting on 43 different events of Table I. Some of the events are classified by the rate of the patient's heart. The heart rate menu option allows the user to specify the heart rate ranges that are used to define the various related events. Event Priorities option allows the user to specify event priorities within each of the three classes of Table I.

TABLE I

Superventricular
Irregular Rhythm, [S.A. vs. AFib]
SVT, Rate 120–150
SVPB
SV Couplet, Triplet
SVPB > 10/min.
Sudden Rate Increase
Nonsustained SVT, Rate > 150
Sustained SVT, Rate 150–180
Sustained SVT, Rate > 180
Atrial Fibrillation Bradycardiac
Rate 50–60
Short Pause
Rate 40–50
Missed Beat (s)
Long Pause followed by SV Beat
Rate < 40
Sudden Rate Decrease
Long Pause with Ventricular Escape
Asystole Ventricular
Fusion/Abbarent Beat
VPB
Trigeminy
Bigeminy
VPB > 5/min.
Couplet
Triplet
R on T VPB
Multiform VPB
Irregular Ventricular Rhythm
Nonsustained VT, Rate < 125
Multiform Nonsustained VT, < 125
Nonsustained VT, Rate 125–170
Multiform Nonsustained VT, 125–170
Nonsustained VT, Rate > 170
Multiform Nonsustained VT, > 170
Sustained VT, Rate 40–125
Multiform Sustained VT, 40–125
Sustained VT, Rate 120–170
Multiform Sustained VT, 125–170
Sustained VT, Rate 170–280
Multiform Sustained VT, 170–280
Ventricular Fibrillation/Flutter The Alpha uses the priorities to determine which ECG strips are most important for a particular patient.

The user may specify how the data will be printed when the procedure has completed. The options of Table II are available. The pre-setting of these options in block 80 allow the Alpha to be connected to any Omega when the procedure has completed. The Omega will use the report options stored in the Alpha to determine the report formatting options that are to be used for this patient.

Real-Time ECG Display 75 is run concurrently with patient set-up 73 when ECG data from the Alpha is displayed on the Omega CRT. The Alpha data is optionally combined with a grid that is displayed on the CRT in such a manner as to simulate the continuous strip chart recording that physicians are assustomed to reading. As the constant shifting of this high resolution graphic data is beyond the capability of the Omega CPU, a special hardware shifter is used to assist in the real-time movement of the ECG trace.

Print Alpha Data 76 memory allows the user to print the results of a procedure. The data may be resident in an Alpha or may have been stored on a floppy disc as the result of a previous procedure. These options make use of the programs 77 "upload" and 78 "get Alpha data" in order to obtain the Alpha data from the Alpha or a diskette.

TABLE II

| Report Options |
|---|
| (A) Arrhythmia Analysis: |
| Hourly Summary |
| Hourly Histograms |
| Major Event Log |
| ECG Strips |
| Summary Period |
| R—R Interval Distribution |
| QRS Forms |
| Hourly Summary by QRS Forms |
| (B) S-T Deflection Analysis: |
| S-T Declection ECG Strips |
| S-T Summary Period |
| (C) Patient/System Interaction: |
| Patient/Marker Summary |
| Protocol Parameters |

The memory allows the following options: (a) Print report from Alpha, (b) Print report from diskette, (c) Save Alpha data on diskette.

Print Report from Alpha reads the data from the Alpha and decompresses it. The data is then placed into report format based on the report options that were defined in the protocol definition. The user is allowed the opportunity to change the report format definition (via block 80) if the one found in the protocol was inadvertently defined incorrectly. After report formatting is completed, the data is plotted on the printer 26.

Print Report from Diskette works exactly as Print report from Alpha, except that the compressed data is retrieved from a diskette instead of an Alpha. All print options are then made available to the user before the data is plotted.

In Save Alpha Data on Diskette, the data from the Alpha is uploaded and is written to a diskette for later printing.

ALPHA

Figure 7:
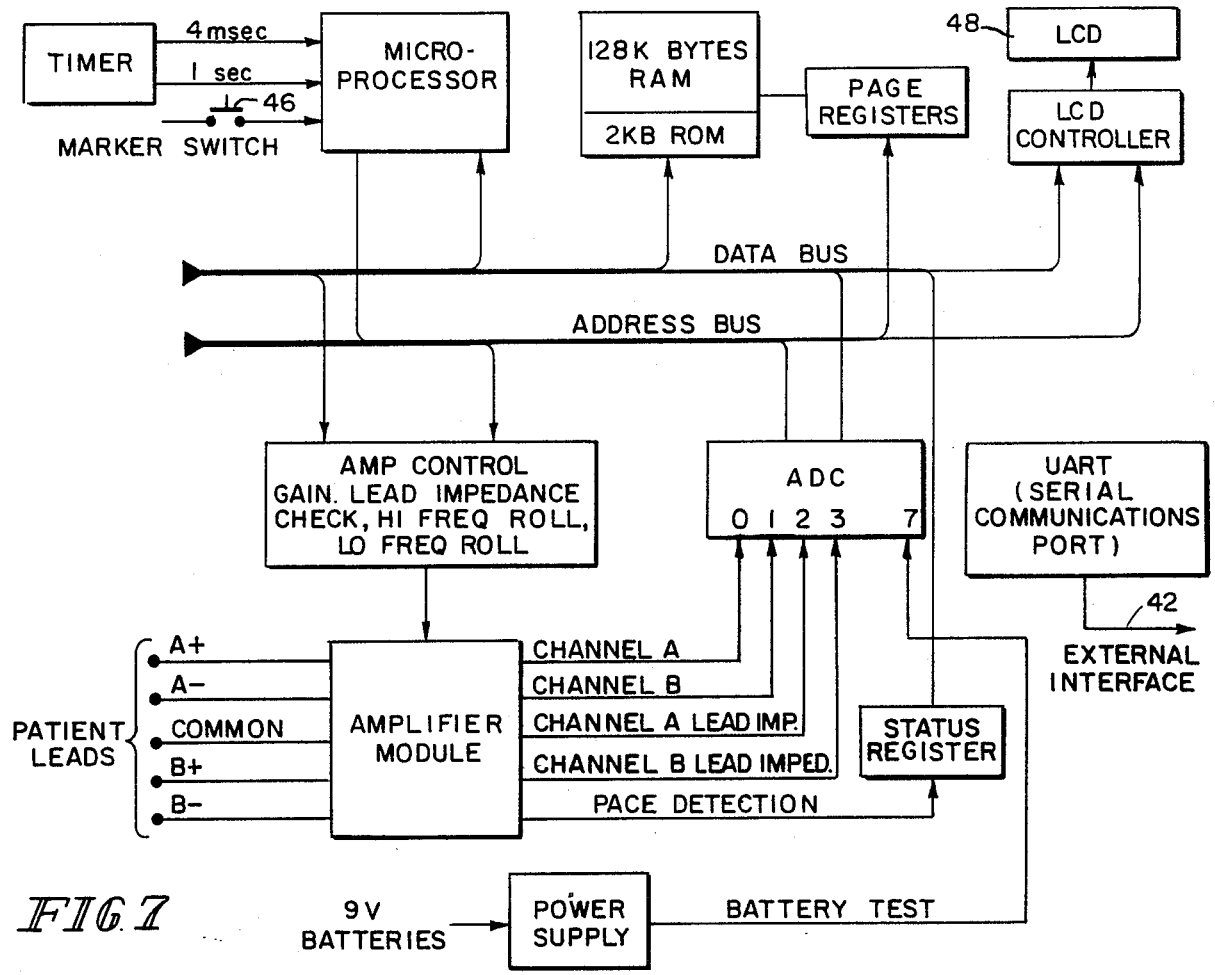
FIG. 7 is a block diagram of the ambulatory ECG analyzer.

The Alpha 40 is a special purpose computer system, specifically tailored to fulfill the requirements associated with ambulatory electrocardiogram monitoring. The Alpha as illustrated in FIG. 7 is configured as a self-contained, battery operated, portable, electronics set, with peripheral device expansion capability. The control program is loaded via a serial communications port 42. The central processor module is composed of an eight bit microprocessor and the associated memory, timing and interrupt control logic. The processor is implemented in a manner to access peripheral devices via I/O Port instructions only. The Alpha memory consists of READ ONLY (ROM) and READ/WRITE MEMORY (RAM). The 2K ROM provides control after power on and performs basic internal diagnostics prior to initializing a loader program. The RAM is comprised of 128K bytes of static memory, expandable to 256K bytes.

A 4 character, 7 segment, Liquid Crystal Display (LCD) 48 with a 0.250 inch character height is implemented to display the time of day and initialization information. Provision is made for one input switch 42 closure to be detected. This is a marker activated by the patient indicating a user activated event of interest. A full duplex serial asynchronous communications channel is provided as a communications interface with the Omega 20 or other external devices, i.e., Modem. The baud rate is determined by an external or internal clock. The internal clock provides for 31,250 baud. The external clock may vary the baud rate up to 38,400 baud maximum. An eight input to digital converter allows the control program to monitor two channels of ECG activity as well as the state of the internal battery supply, and (patient) lead impedance.

The analog circuitry provides for the connection of external ECG leads, with testing for lead faults.

The Alpha is powered by two 9 volt batteries and may be placed into a data retention mode (minimum power consumption).

The CPU is an eight bit microprocessor capable of directly addressing 64K bytes of main memory. All peripheral devices are implemented as I/O ports. The ROM consists of 2048 bytes of CPU addressable memory occupying logical locations 0000(hex) to 07FF(hex) while the ROM disable Flip Flop is reset. The CPU will, as a result of power on reset, reset the ROM disable Flip Flop and commence instruction execution from location zero. When the ROM disable Flip Flop is set, the ROM is no longer accessible, and the first 2K of RAM is addressed as logical locations 0000(hex) to 07FF(hex).

Figure 8:
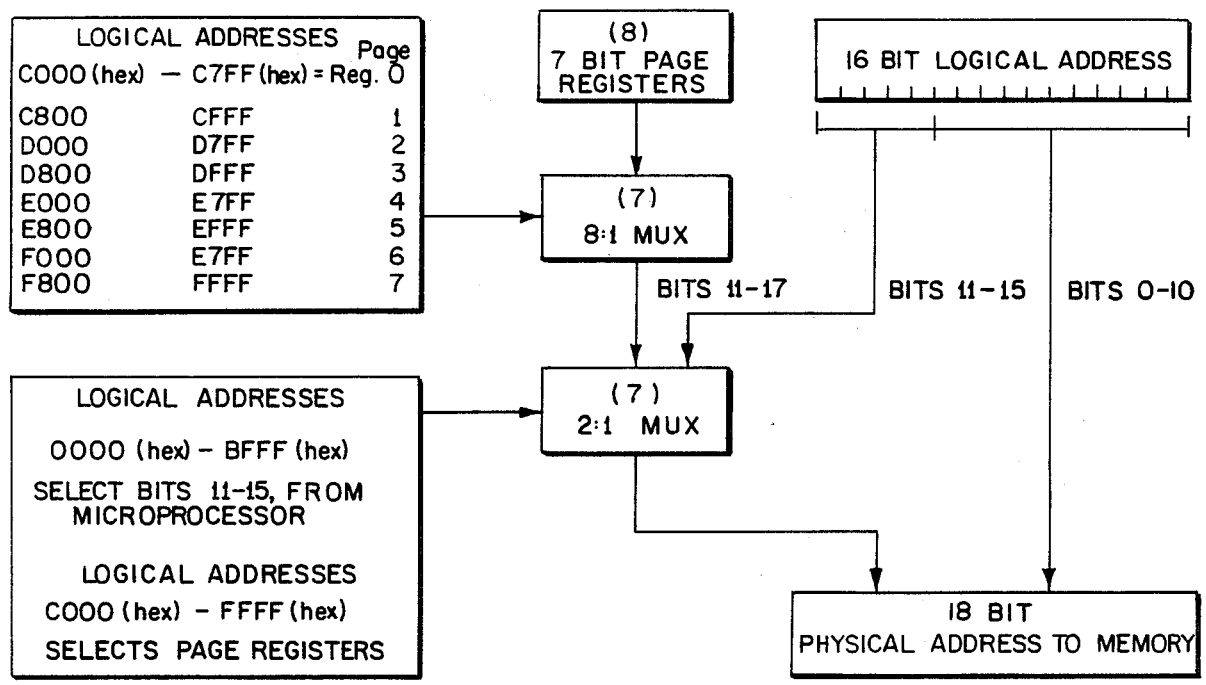
FIG. 8 is a block diagram of memory addressing for the abulatory ECG analyzer.

A processor memory map is shown in FIG. 8. The physical RAM consists of 128K bytes with 48K bytes (locations 000(hex) to BFFF(hex)) having a direct logical to physical correspondence. The remaining 16K segment (C000(hex) to FFFF(hex)) may access any of the 128K bytes as 8 pages of 2K bytes per page by performing a logical to physical translation through the page registers.

Figure 9:
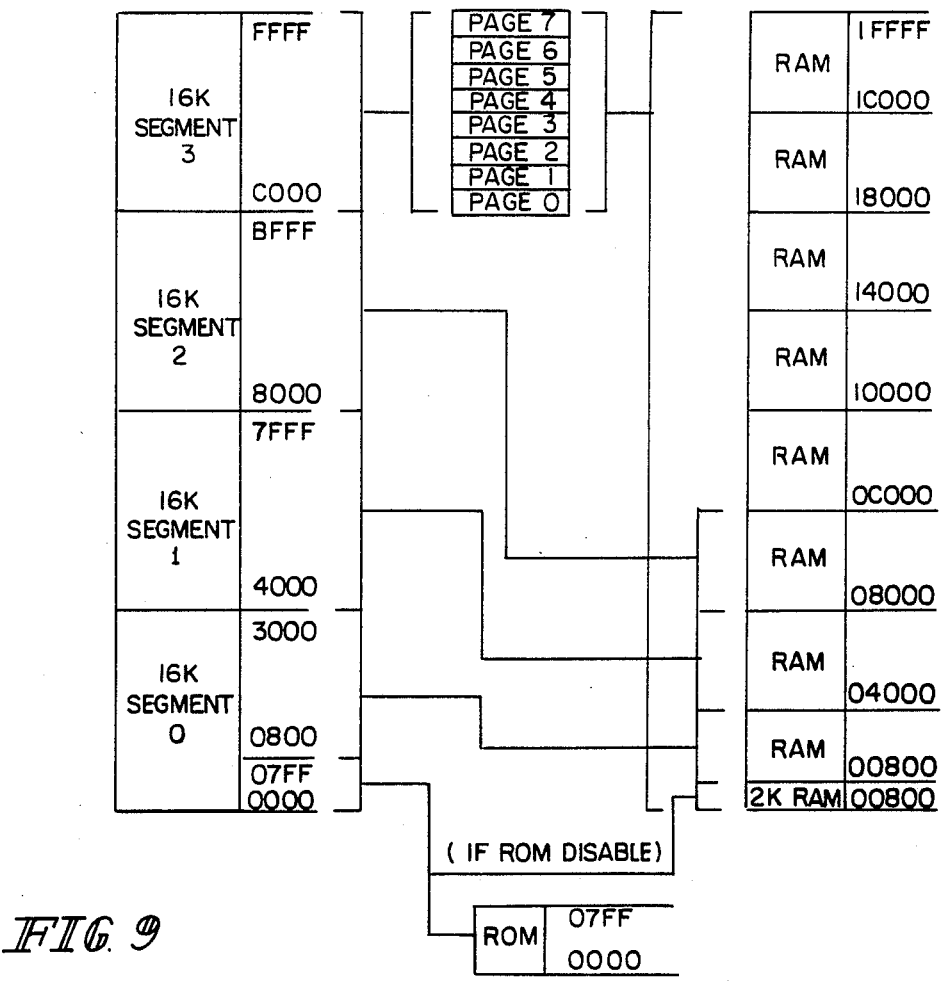
FIG. 9 is a block diagram of page mapping.

Eight page registers select eight 2K byte-pages to be accessed as logical address c000(hex) to FFFF(hex). Logical address C000(hex) through C7FF(hex) translates through page register zero, C800(hex) thru CFFF(hex) translates through page register one and etc. The page registers illustrated in FIG. 9 are loaded as I/O devices. On power up, the page register contents are undetermined.

The interrupt structure is such that the processor will vector to the correct address for each interrupt occurrence. All interrupts, with the exception of the 4 ms timer, are maskable by the disable interrupt instruction. The 4 ms timer interrupt can be disabled through an I/O port. Five interrupts are provided. The interrupts in order of priority are 4 ms timer, 1 sec timer, serial interface (UART), analog to digital converter (end of conversion), and the switch closure or Diary data in.

A 4 character (7 segment) LCD display allows direct display of numeric data. The display controller performs the required character refresh. The display is written via I/O port addresses. The controller displays 4 characters with a character set of 0-9, dash, E, H, L, P, and blank.

The Alpha system has one user switch 46 (marker). The switch closure generates a vectored (Mode 1) interrupt to location 0038(hex). The interrupt is generated upon switch closure. The switch interrupt may be enabled or disabled by writing a one or zero to the switch interrupt control flip flop.

The Alpha incorporates a full duplex serial communication channel for docking with the Omega system. The baud rate is determined by the clock supplied by the Alpha (31,250 baud). Four individual registers control the serial interface.

The control register configures the serial interface regarding bits per character, parity, and stop bits.

The status presents possible error conditions and the state of both transmit and receive registers. Reading of the status register resets the interrupt. The "ES" bit is used as a "Docked" status bit.

The byte written into the transmit register is output in serial fashion to the external device. The byte transmitted by the external device in output from the receive register.

An interrupt generated by the serial interface, occurs as a restart B (Address 0034(hex)), and is reset by reading the status register.

The analog to Digital Converter (ADC) converts one of eight input voltages to a binary (8 bit) value corresponding to that voltage. An interrupt is generated (restart C, Address 002C(hex)) at the completion of the conversion. The interrupt is reset upon reading of the ADC data.

The input of the ADC is selected by a write to the selected channel address. Writing any data into the selected channel address initiates the conversion, and a processor interrupt is generated upon the conversion completing.

The ADC channels are shown in Table III below:

TABLE III

| CHANNEL | FUNCTION |
| --- | --- |
| ADC Channel Select 1 | Output Channel A |
| ADC Channel Select 2 | Output Channel B |
| ADC Channel Select 3 | Fault Test Channel A |
| ADC Channel Select 4 | Fault Test Channel B |
| ADC Channel Select 5 | Reserved |
| ADC Channel Select 6 | Reserved |
| ADC Channel Select 7 | Reserved |
| ADC Channel Select 8 | Battery Test |

Figure 10:
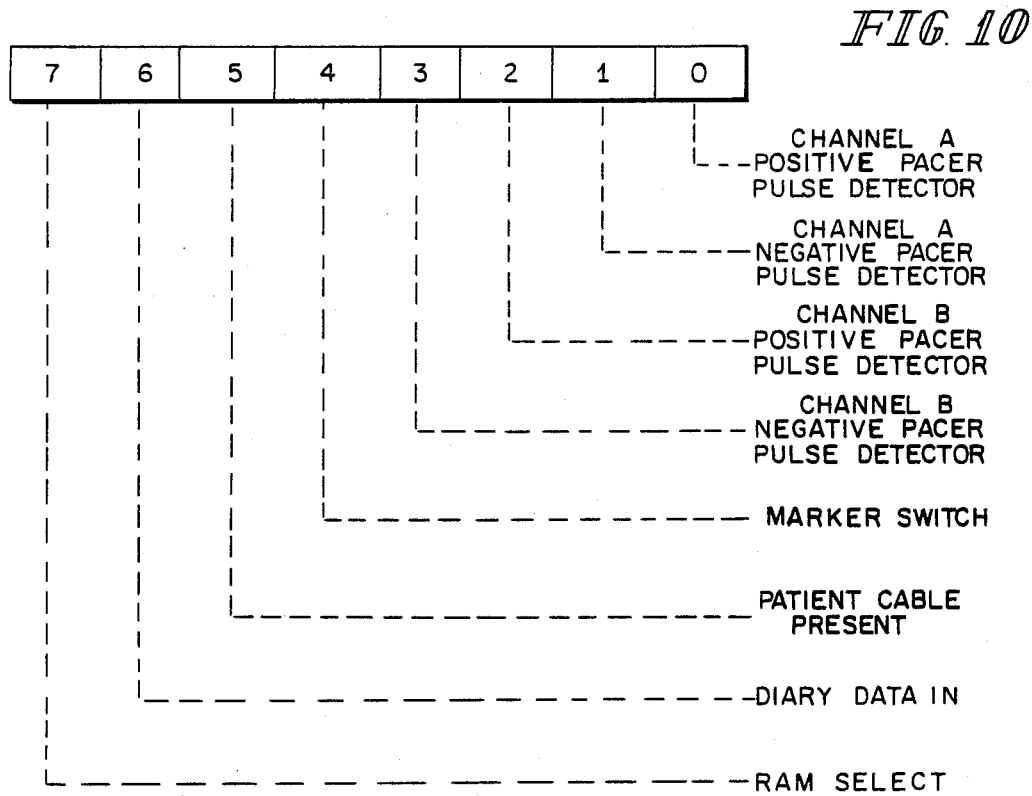
FIG. 10 is a status register.

An eight bit register is implemented to access miscellaneous status information. The register bit assignments are shown in FIG. 10. The register (read only) is accessed via an I/O port. Four status bits (two per channel), when set to a one, indicate that a positive or negative (or both) pacer pulse has been detected on the associated channel. The Marker Switch bit is set to a one whenever the marker switch 46 is being depressed. The Patient Cable connected bit is set to a one indicating the Patient Cable is connected to the Alpha 40. The Diary Data In bit is the serial data coming in from the Diary unit 60. The Ram selected bit is set to a 1 when the RAM is selected, and set to zero when the ROM is selected.

The Alpha system utilized two power conservation modes to extend battery life. Writing any data to the Power Save 1 flip flop will cause the NSC-800 to be placed in a halted state. Any interrupt condition will reset this mode and permit the control program to resume execution. This mode is reset as the result of power on reset.

Writing a one to the Power Save 2 flip flop will disable all Alpha circuitry except the RAM and cause the voltage to be reduced to 3V to allow maximum power conservation while maintaining the data in RAM. The bit is reset only by an external reset.

A selectable 2 msec or 4 msec timer interrupts the processor via the non-maskable interrupt (vector 0066(hex)). This interrupt is disabled (inactive) as a result of a power on reset (or a reset from the Omega system). It is enabled by writing a one into the Enable/Disable port, and can be disabled by writing a zero into the same port.

A one second timer interrupts the processor via the restart, an interrupt (vector 003C(hex)). This interrupt can be disabled with the disable interrupt (DI) instruction or by resetting the appropriate interrupt mask bit in the processor.

Four lines (plus ground) make up the Alpha-Diary interface. A separate connector is provided for this interface.

The serial data that is transmitted from the Diary unit 60 to the Alpha 40 is brought in as a bit in the status port. Writing a one into the Interrupt Enable Port will allow high-to-low transisions of the incoming data to generate an interrupt (vectored to 0038(hex)). This interrupt is shared with the marker switch 46. In addition to clearing the interrupt, reading the status will cause a read strobe to be generated, which is used to indicate to the Diary unit 60 that the Alpha 40 has accepted the bit and is ready for the next bit. The serial data transmitted from the Alpha 40 to the Diary unit 60 is written to the Diary Data Out port.

Each time a bit is written to this port, a write strobe is generated which will indicate to the Diary unit that a bit is ready to be accepted. The Write Strobe, an active low pulse is generated each time a bit is written to the Diary Data Out port. It is used to indicate to the Diary unit that a bit of data is ready for processing. The Read Strobe, an active low pulse is generated each time the status register is accessed via port 60 (hex). It is used to indicate to the Diary unit that the Alpha has accepted the data bit and is ready for the next.

The Alpha amplifiers are twin parameter-programmed circuits for amplification of the ECG signals described in U.S. patent application Ser. No. 441,175 filed Nov. 12, 1983, now U.S. Pat. No. 4,494,551, to Little and Patterson titled "Alterable Frequency Responsive Electrocardiographic Amplifier," which is incorporated herein by reference. Control of gain, upper frequency cutoff, and lower frequency cutoff is provided for each channel independently via the amplifier control ports. Additional control ports allow for the direct measurement of electrode impedance, ports are described in Table IV. Fifteen one-bit (write only) registers control the functions of the amplifier circuitry.

TABLE IV

| Amplifier Control Registers |
| --- |
| FUNCTION |
| Channel A Gain Lo |
| Channel A Gain Hi |
| Channel A Fault Test Select Lead #1 |
| Channel A Fault Test Select Load #2 |
| Channel A Upper Frequency Limit Control |
| Channel A Lower Frequency Limit Control |
| Channel A Pacer Detect Hold Control Enable |
| Lead Fault Test Toggle Bit |
| Channel B Gain Lo |
| Channel B Gain Hi |
| Channel B Fault Test Select Lead #1 |

TABLE IV-continued

Amplifier Control Registers

Channel B Fault Test Select Lead #2
Channel B Upper Frequency Limit Control
Channel B Lower Frequency Limit Control
Channel B Pacer Detect Hold Control Enable Five amplifier control registers are utilized to implement the electrode test function. Four ports select the electrode lead to be tested and one port enables the test value to be processed by the ADC.

LEAD IMPEDANCE

Electrode lead impedance is determined by measuring the voltage swing produced by a fixed test current in each lead. This voltage is directly proportional to impedance of the connection.

Figure 11:
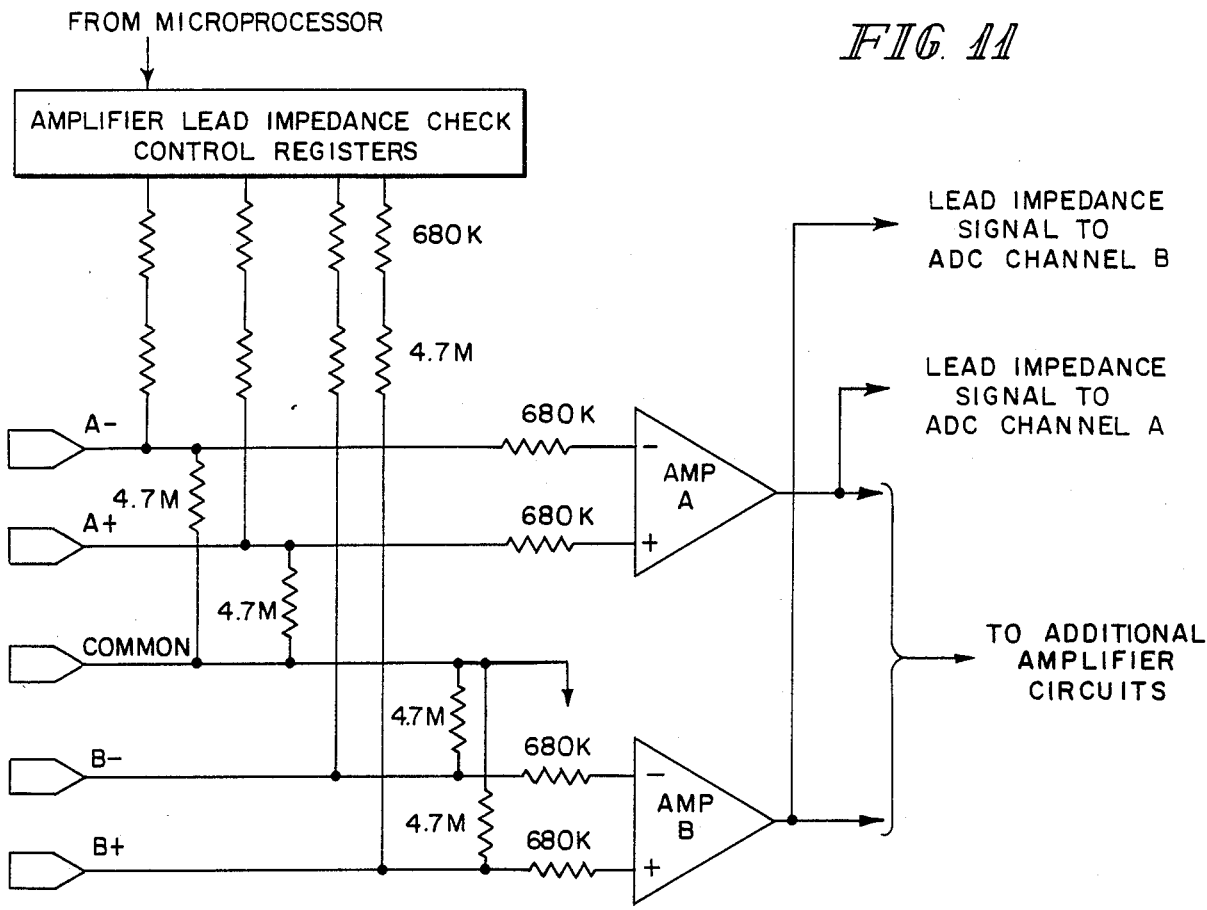
FIG. 11 is a schematic of the lead impedance test circuit.

As shown in FIG. 11, dual amplifiers are connected via five conductors to the patient. Impedance Check Control Registers drive high-value resistor pairs to each lead (except Common) from tri-state buffers. During normal QRS signal monitoring, the Register buffers are set to the high impedance state. This open circuit condition removes these resistors from the circuit.

During an impedance measurement, one of the Register buffers is switched to low impedance and a square wave signal is output. The square wave frequency is programmable and swings symmetrically about the common connection. Any resistance appearing in the electrode-skin contact will produce a voltage drop. The voltage signal occurs at the ECG amplifier input so that an amplified signal is output to the Analog-to-Digital Converter (ADC). Peak voltage excursions are sampled and substracted to determine the net voltage excursion. This value represents the impedance of the lead under test. It should be noted that voltage drop through the Common lead appear as a common mode signal and hence is not amplified. This procedure is repeated for the other three leads.

PACEMAKER DETECTION

When present, pacemaker spikes are a high frequency component of the QRS waveform. The rise and fall time for such spikes are typically 100 times faster than any biological transients. Pacemaker spikes are detected by preferentially amplifying high frequencies with a differentiator, then triggering a comparator when a fixed, threshold is exceeded.

Figure 12:
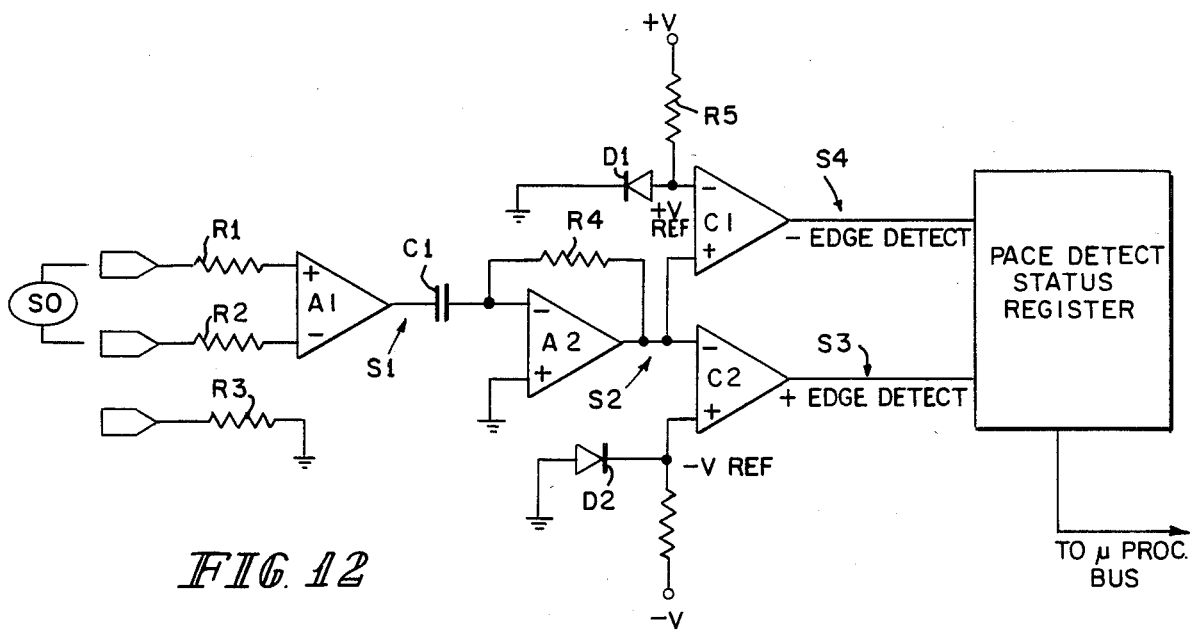
FIG. 12 is a schematic of the pacemaker detect circuit.
Figure 13:
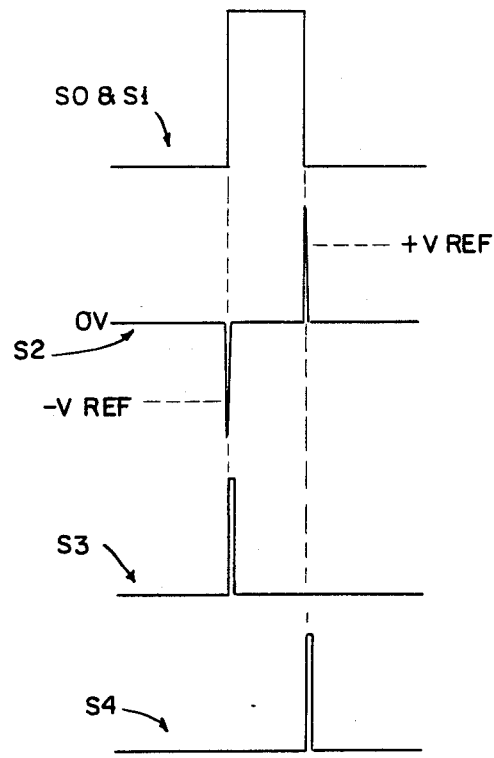
FIG. 13 are waveforms at various points of FIG. 12.

FIG. 12 shows the pacemaker detection circuit. Amplifier A1 receives the composite pacer-QS signal from the chest electrodes, boosting it to a usable level for later processing. The output (SI) is differentiated by amplifyer A2 to magnify high frequency components. As shown in FIG. 13, short spikes representing each edge of the pacemaker signal are produced. These are then compared to fixed positive and negative reference voltages (+V ref and −V ref) with voltage comparators C1 and C2. When the reference voltages exceeded, logic transitions are produced at the comparator outputs (S3 and S4). These signals, in turn, trigger logic circuitry which indicate pacer detection to the microprocessor bus.

ALPHA OPERATION

Figure 14:
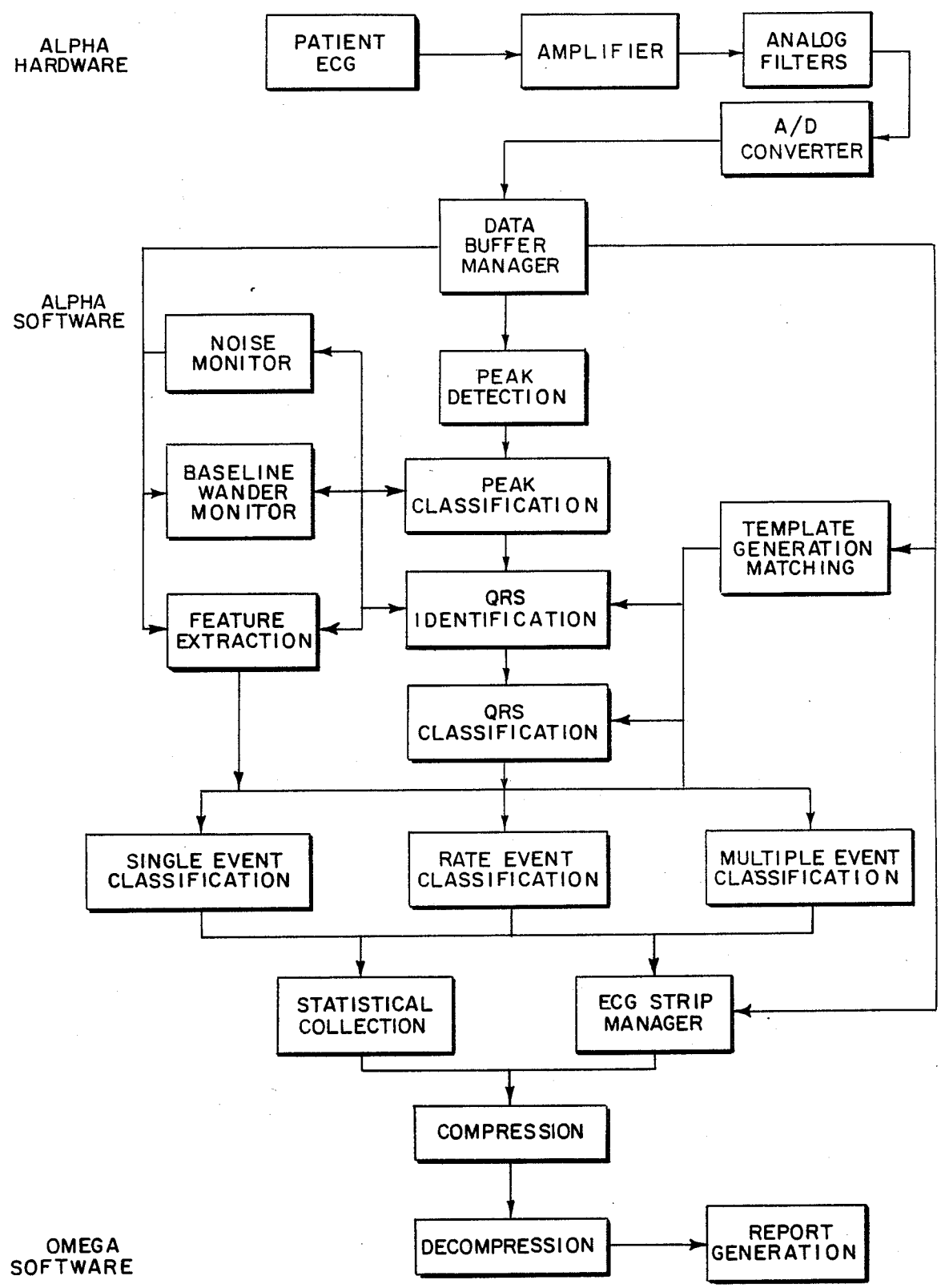
FIG. 14 is a diagram of a software of the ambulatory ECG analyzer.

Analysis of the two ECG channels as illustrated in FIG. 14 is controlled and managed by the control logic using a pair of windows sliding in tandem through the ECG data in time. These windows enable the control logic to extract necessary information from the ECG in each channel and provide the framework to correlate the information. As the old ECG data within these windows is completely analyzed, the windows are contracted on the left to release the analyzed ECG data and make room for the new data.

The process of identifying QRS complexes and classifying them as typical/atypical is performed in three major steps using input signals in both channels and coorelating the results:

a. Peak collection: All peaks in the ECG windows are detected using a peak detector and are classified by delineating and extraction of various features and other parameters which are stacked up as pairs in time.

b. QRS Identification: After having collected all the peaks in the window, real QRS complexes are identified, selected, artifacts rejected, and small QRS's are detected using low threshold scans.

c. QRS classification: Identified QRS complexes are classified as typical/atypical using a combination of template matching and feature extraction techniques applied in tandem as well as in a hierarchial fashion.

Information regarding the classifier QRS complex is supplied to the event classifiers, ECG strip manager, and statistical collector routines to perform appropriate operation at the tail end of the loop. This process is repeated as the ECG windows are slided forward in time.

As will be evident from the following description, the present system is capable of making more accurate decisions faster by centralizing the decision making process. This allows performing a plurality of data and signal analysis only when needed and maintaining the analysis information for later decision.

ECG Data Collection and Buffer Management:

Patient ECG is sampled at 250 hz on each ECG channel. Each ECG sample is eight bits wide. Sampled ECG data is put into a circular buffer by the data buffer manager. This is done so that when enough contiguous data is available, ECG analysis could be performed. In general, the ECG analysis process will be running faster than the ECG data acquisition rate. Consequently, it will be waiting for sufficient ECG data to accumulate before analyzing it. Moreover, the process of buffering the data enables the software to analyze one piece of ECG while next piece of ECG is being collected. ECG data acquisition is performed on a priority basis regardless of any other activity in the Alpha unit.

To understand the operation of this logic, let us assume that at a given point in time, we have just finished classifying some QRS complexes on the left hand side (earlier in time) of the window. After the QRS classification has been completed, the logic removes the old data from the window by contracting the left hand side of the window. This makes the window smaller than its max size, permitting us to expand it on the right hand side (later in time). This process of contraction and expansion, in effect, simulates the sliding of the window through the ECG data in time.

Realizing that the window is not at its maximum size, the peak collection logic which includes peak detection and peak classification obtains more data and expands the window on the right hand side. If sufficient data is not available, this logic waits for the data to arrive. Once sufficient data is available to expand the window, this logic proceeds further. The process of window expansion is performed in small steps rather than one big step. This allows the logic to start working on the small chunk of data obtained while the next chunk is being collected. This allows better utilization of the available processing time rather than wasting it while all of the larger chunks of data are being collected.

Peak Detection:

Peak detection has been implemented in software. It is based on simple first difference approach. It examines the variation in amplitude between a sample and the sample seven points before it. If the difference in amplitude exceeds a certain predetermined threshold, a peak is considered to have been detected. The threshold used by the peak detection logic is initially established during patient initialization process. Thus, it is not a fixed quantity, but instead is patient dependent. It is determined from the overall amplitude of the patient's typical QRS complex.

The peak detection threshold is adjusted dynamically during the procedure. This is done to allow for the variation in the QRS amplitude with respect to respiration, body posture etc. This is accomplished by computing a running average of QRS amplitudes and using the average amplitude to determine the threshold. Thus, there is a feedback loop to dynamically adjust the threshold as new QRS's are detected and identified. This makes the system adaptive to the variations in patient ECG during the analysis period.

Our approach has been to not fine tune it. Instead of fine tuning the threshold, the present system uses two different thresholds to detect QRS complexes. During the first pass over the data, a high threshold is used to pick up, hopefully, only QRS complexes. This threshold is sensitized to picking up typical QRS complexes. However, this may result in missing small QRS complexes. This problem is circumvented by using a low threshold detection in the same region whenever it is necessary. This decision is made by the QRS identification logic. When it sees a long region of ECG without any QRS complexes, it suspects a peak detection failure and uses the low threshold to pick up any small QRS complexes.

Moreover, the approach of analyzing two channels continuously makes the QRS detection process more accurate. This is due to the fact that the probability of a QRS complex being small in both channels is much lower than it being lower in one channel. Our approach of continuously analyzing two channels and correlating their information makes it very sensitive in QRS detection.

Peak Classification, QRS Identification, and QRS Classification:

This portion of the system consists of a central control logic module and a number of support modules dedicated to a certain fixed function.

The function of the control logic is to invoke all other system modules as when necessary. Invocation of each module requires supplying them with necessary input parameters to accomplish their function. Control logic provides these necessary parameters to them and also receives information from these modules. This information received from various modules is assembled and assimilated by the control logic. It uses this information to make various decisions, e.g.,:

a. whether a detected peak is a QRS complex or not.
b. whether a QRS complex has been missed or not.
c. how to correlate the information from both channels.
d. how to control the scanning process of each channel.
e. determine whether channel is exhibiting excessive noise and/or baseline wander or not. If it is, put it in shut-down state and monitor it until the signal is acceptable for further QRS analysis.
f. determine the type, i.e., typical or atypical, of a detected QRS complex. This decision is made by correlating the information obtained from feature extraction and template correlation techniques.
g. determine whether a channel is exhibiting very small signal to accomplish accurate QRS detection and identification. If it is, put it in a low amplitude state and monitor it until signal is once again acceptable for further analysis.
h. use the ECG contexual information to make various decisions.
i. use the information from previously analyzed QRS to further aid in detecting and identifying future QRS complexes. This makes the logic adaptive and imparts intelligence to it, i.e., it learns as it goes on.

This approach of using a centralized control logic module to make final decisions in QRS identification and classification paves the way for a very accurate, robust, adaptive QRS detection and identification process. This is due to the fact that emphasis is now shifted away from making each support module being very intelligent and accurate. With a centralized decision making approach, information from each module is collected and combined with information from other modules to make the final decision. Thus, it is possible to use two different approaches to achieving the same function. For example, both feature extration and template correlation techniques can be used to classify (typical/atypical) QRS complexes. Information from both techniques can be correlated and a final decision can be made. This process of combining intelligence from more than one approach results in each approach complementing the other. Weakness of one approach could be the strength of other and vice versa. Thus, overall accuracy will be much higher.

In order to facilitate the simultaneous analysis of two ECG channels, information from both channels is always processed and stored in tandem or pairs. Furthermore, to facilitate the ECG analysis of two channels, one channel is designated as the primary channel and the other is designated as the secondary channel. The primary channel assignment is dynamic and is changed as the quality of the signal improves or deteriorates in either channel. This makes the logic adaptive to the changes in ECG.

A search is made in the primary channel for peaks in the new data appended to the window. If no peak is found, window is further expanded, up to its maximum size, and the search for peaks is continued. Once a peak is found in the primary channel, the next step is to delineate the peak and extract various features for the potential QRS complex. Along with the feature extraction process, a number of measures representing the quality of the peak and its delineation are also collected. This information is later used in correlating two channels and rejecting artifacts, etc. The quality information gathered includes things like: too wide, too narrow, very small, unstable i or j point, very small T-wave, etc.

Peak Classification:

To facilitate further analysis, each peak is classified and assigned a tag consisting of one of the following five symbols:

a. M: peak matches a typical model.

b. H: peak did not match the typical model, but was picked up at high threshold scan.
c. L: peak did not match the typical model but was picked up at low threshold.
d. S: peak did not match the typical model, but there was excessive noise and/or baselines in the region of the peak. Thus requires that the channel be shut down for ECG analysis.
e. A: No peak was found or a bad peak (two narrow, too wide, very small, etc.) found.

The rationale behind this kind of tagging is to provide an orderly analysis of different kinds of information seen in ECG and further aid the selection and classification process using coexternal information. This technique provides a convenient way to examine ECG context.

After delineating a peak as a potential QRS complex, the control logic determines whether this could be a typical beat of the patient. This is determined using a typical beat detection module in the feature extractor. This module maintains a description of the typical beat of the patient. This is called the typical model. The potential QRS complex under scrutiny is compared with this model using the features extracted for it. A numeric value is assigned to the results of the comparison. The comparison process employs various tolerances for different features. After determining, in a quantitive fashion, how different a beat is from the typical model, a decision is made by the control logic to make a preliminary classification for the beat as typical or atypical. Once again, the decision is only preliminary and sufficient detailed information is saved to make a final decision at a later point when other information is also available.

The typical model maintained by the typical beat detection module is dynamically adjusted as new typical beats are detected. This makes it adaptive and less vulnerable to errors caused by changes in QRS due to respiration and body posture.

If a peak is not assigned an M tag, it implies that the beat is an atypical beat, an artifact or a typical beat obliterated by noise/baseline wander. To make the proper determination, it is necessary to measure noise/baseline wander. At this stage, noise and baseline wander are estimated. If either or both are found to be excessive, the peak is assigned a S token and the channel is put in a shut down state. This state indicates to the control logic to process it differently in future until the signal gets better to be useful for proper analysis.

If noise and baseline wander are better or absent, the peak is assigned the H or L tag based upon the threshold used in picking up the peak.

Making noise and baseline wander measurement only when we have failed to find a typical beat is geared towards making the system efficient since noise and baseline wander are typically very time consuming tasks. Consequently, performing them on ongoing basis will consume large amounts of power and time.

The noise monitor derives a quantitive measurement for the high frequency noise content of the signal. This is achieved by selecting the region around the peak in a window and subdividing the window into subregions. Each subregion is then examined for high frequency noise content. This is done by computing first differences and comparing them against certain thresholds. Depending upon the number and type of threshold crossings found a noise grade, i.e. high, medium, low, is assigned to the subregion. Noise grades from various subregions are then combined in a weighted fashion to derive the final noise grade for the entire region under scrutiny. This information is supplied to the control logic to make its decision on whether there is noise or not, and if there is, is it high enough to shut-down the processing of the channel until the signal quality improves in the ECG channel. This information regarding the noise is also saved for later use in determining the quality of an ECG strip for selection in the report.

In two channel analysis systems, noise/baseline wander in one channel does not shut down the entire analysis process because the other channel may have a noise/baseline wander free signal and the computer can continue to detect and identify beats in that channel. The probability of having noise/baseline wander on both channels simultaneously is much lower than noise/baseline wander on one channel. Consequently, a two channel analysis sytem will have much smaller shut-down time.

Baseline wander monitor is invoked by the control logic in conjunction with the noise monitor to determine if the low frequency baseline changes, motion artifacts, or sudden baseline changes are obliterating the QRS complex or not.

This is achieved by first filtering out the high frequency content, including the QRS complex, from the signal and examining the remaining low frequency content of the signal. The low frequency content is evaluated for drifts and a baseline wander grade, i.e., high, medium, or low, is assigned. This grading is combined with a secondary grading obtained by comparing the computed baseline of the QRS complex with the averaged baseline of the preceeding QRS complexes. This secondary measure allows the system to pick up sudden baseline shifts and complements the primary measurement and thus improves its accuracy.

If excessive baseline wander is detected, the control logic will shut down the channel exhibiting the baseline wander and monitor it until the signal quality improves.

After picking up the peak in the primary channel and assigning it a proper tag, the next step is to analyze the secondary channel to find the corresponding information in it.

The area surrounding the primary channel beat is projected into the secondary channel and that particular area in the secondary is searched for a peak. The entire process of picking up a peak and tagging it is repeated here. If no peak is found at high threshold, an immediate rescan is made in the same region at low threshold. This attempts to extract information in the secondary channel to match up against the already obtained information in the primary channel. The low threshold scan information is needed for immediate correlation of two channels.

At this stage, a peak pair combination consisting of any two symbols from the five symbol alphabet described before is possible. This starts building some contextual information and starts the two channel correlation process.

It should be noted that the secondary channel was not contiguously scanned from a previous scan point. Instead, the intermediate region was skipped and the system went straight to the area of interest as indicated by the primary channel. Since the ECG in two channels is coming from the same source, there must be very close temporal relationship and synchrony between the two channels. Moreoever, most of the time a [M, M] combination is expected in two channels. Thus, having found one channel's peak, the system knows where to scan for other channel's peak. This saves time and keeps the information in two channels in tandem.

Whenever an M is found in the primary channel and a non-[M, M] combination is found, it is used as and indication of need for caution. Consequently, the region of the secondary that was skipped is now scanned at high threshold. For the purpose of this scan, the secondary becomes the primary and vice versa. Once again we may obtain zero or more peak pairs in this process. Since these peak pairs occur, in time, before the peak pair picked up initially, the list is adjusted to put them in proper place to maintain the contextual information. Having started such a contiguous scan of the secondary channnnel, the control logic will continue it in future until a [M, M] pair is found. The rationale being, a [M, M] signals that we are on familiar territory once again. In any case, the control logic always maintains precise information on what regions of which channel have been scanned at what threshold. This prevents costly rescans at a later time.

The input signals are contiguously scan before and after a non-[M, M] pair, because the peak pair may be misaligned, or we just have a piece of a QRS in either or both channels, or there is noise or baseline wander in one channel that is causing the M to become non-M, but is it not large enough to be picked up by noise/baseline wander monitor. In many instances, such noise/baseline wander can be easily picked up by looking at the region before or after the peak. This will allow the system to shut down the channel appropriately.

After obtaining a peak pair, the next step is to establish its quality by examining the information in both channels. A number of artifacts can be identified at this early stage. Since many of the artifacts affect only one channel and show up as [X, A] or [A, X] (where X is a M, H, L or S) combinations. These are very suspicious combinations. Such combination indicate that one channel says there is a peak and others say there is none. There is an obvious conflict here. Sometimes this may be genuine peak pair representing a QRS. This happens when the QRS is iso-electric in one channel and not in the other channel. Most often, however, this is an artifact. This combination also occurs when the signal becomes very small in one channel or there is a complete loss of signal in one channel. In any event, to make the proper determination, some of the factors considered for rejecting some artifacts are:

a. type and size of the peak in the channel exhibiting the peak.
b. size of that peak compared to the average size being observed presently in that channel.
c. average size of beats being observed in the channel with very low peak or no peak or bad peak.
d. size of the small peak compared to the average peak size in that channel.
e. size comparison of two peaks.
f. time relationship of this peak pair with respect to the nearest peak-pairs.

Once a determination is made to reject the peak pair as an artifact, it is not rejected right away. Instead, it is tagged for rejection for a later stage. This allows a later reversal, if necessary, of this decision by other criteria.

This artifact rejection technique based upon peak-pairing approach provides a very powerful tool. For example, consider the case of ECG where the P-waves are comparable or larger than the QRS complex. A single channel system in such cases will be trying to decide on whether to keep the P-wave or the QRS following it without very solid information to go on to make this decision. However, with a two channel system, the probability of this happening in both channels is very low. Consequently, the P-wave will be picked up as an [X, A] or [A, X] combination. Moreover, it will be picked up close to a [X, X] combination representing the real QRS pair. Based on this contextual information and criteria described above, the P-wave can be easily rejected. Same thing can happen with large T-waves. Artifacts affecting one channel, which is normally the case, will be rejected by similar reasoning.

If one channel is exhibiting very small signals, it is considered to be in a low amplitude state. This is determined by monitoring the amplitude of successive beats obtained from that channel. When a trend towards very small beats is observed, the channel is put in the low amplitude state. When trend reverses, it is taken out of that state. If a channel is in such a low state, peaks obtained from such a channel are de-emphasized at the peak collection stage to prevent improper selection and classification. This is necessary because when QRS complexes become very small, the ability to discriminate them from one another and to pick M's is reduced. Hence, a H/L on the good channel and M in the low amplitude channel does not necessarily imply that the good channel is supplying improper information. Hence, it is necessary to apply some sort of screening under such circumstances.

Another aspect of two channel information correlation considered at this stage is the alignment of peaks in two channels. Some misalignment of peaks is expected due to projections on two different axis being different. However, when the amount of misalignment exceeds certain thresholds, it is an indication of some problem. Typical problems picked up by this technique are large P waves, large T waves, incomplete delineation, etc. In case of large P or T, the QRS in other channel gets paired with them. However, this results in larger misalignment. Most of the time, in the same region, a nicely aligned pair with peaks in both channels is also found with the misaligned pair. This allows the misaligned pair to be rejected. In case of incomplete delineation in one channel, the delineation is reattemped in the second channel using the information obtained from the good channel. A single channel system cannot obviously perform this kind of refinement.

Shutdown Processing:

As discussed earlier, a channel is shut down when excessive noise/baseline wander is detected. Once a S is found in a channel, it is put in a shutdown state and monitored differently. This shutdown may be very short, one beat, or very long. The objective now is to monitor the signal quality and determine when it is good enough to start QRS analysis. This is achieved by using the non-shutdown channel as the guide. It is now made as the primary channel, if not already assigned as such. Its processing goes on in the normal fashion. However, the shutdown channel is tracked along with it from a noise/baseline wander standpoint. Whenever a peak is found in the good channel, corresponding region is evaluated for noise/baseline wander. If excessive noise/baseline wander still persists, the shutdown is continued. However, if it is low enough, peak detection is employed. If successful, the peak pair is examined. If the shutdown channel exhibits a M, it is allowed to exit the shutdown state and normal processing resumes. However, if it is an H or L, a further determination is made whether this beat pair has been seen before. This is determined using the template matching technique employed by the template matching routine. If seen before, we feel confident about exiting the shut-down state and start using the channel for further analysis. If not seen before, the channel is not allowed to exit the shut-down state. However, the logic remembers that this situation has happened. If this happens, sufficient times without any further episodes of noise/baseline wander the channel is ultimately allowed to exit the shut-down stage.

Above mentioned strategy is modified slightly when both channels exhibit noise/baseline wander simultaneously, a relatively rare occurrence. In such cases, since there is no good channel to use as a guide, both channels are contiguously monitored for excessive noise/baseline wander. As soon as one or both get better, peak detection is employed and the channel(s) is allowed to exit the shutdown state if a known beat or an M found in it. If sufficient successive unknown beats are found, the channel is also allowed to exit the shut-down state.

Identification:

This logic determines which of the detected peaks, i.e., potential QRS complexes, are real QRS complexes and further reject artifacts. It also determines when there is a possibility of having missed a small QRS complex during the high threshold scan. In such instances, it directs the logic to search the ECG channel with a lower peak detection threshold.

The control logic, using various modules discussed above, detects and collects all the peaks, i.e., potential QRS complexes in a certain region of ECG in each channel. All the information produced and supplied by various modules is stacked up for the decision making process. In the process of collecting these peaks, the control logic also performs the critical task of controlling the simultaneous and continuous analysis of both ECG channels. Information from both channels is correlated constantly and is used to control the ECG analysis process in both channels. It attempts to pair beats from both channels and in the process of doing that performs some amount of artifact rejection. When all the peaks in a region of ECG have been detected, the control logic switches to the QRS identification logic to select real QRS complexes from the collected set.

With the information collected by the control logic, the QRS identification logic proceeds to select real QRS complexes. It accomplishes this function based upon a number of rules. These rules use all the information collected by the control logic along with the contextual information in the ECG. The contextual information includes the ordering of and distance between various peaks and their morphological information, patient's average heart rate, refractory period estimates based upon average heart rate, etc. During the artifact rejection process, the QRS identification logic also uses the template matching and generation module to determine if the questionable beat or artifact has been seen before. The probability of seeing the same artifact more than once is very low. Also, the probability of seeing an artifact simultaneously in both channels is much lower than seeing the artifact in one channel.

The QRS identification logic performs its task by first recognizing various possible peak-pair sequences and then taking appropriate action in each case. Different rules can be applied for different peak sequences. For the purpose of this analysis, peak pair sequences are divided into three broad categories:

a. peak-pair sequences ending with a peak-pair containing at least one M.
b. peak-pair sequences with no M in them in the entire window.
c. no peak-pair in the window.

Peak Pair Sequences Ending With At Least One M:

These sequences may contain zero or more non-M peak-pairs before the peak pairs terminating the sequence. If there are any peak-pairs before the terminating peak-pair, most probably they are atypicals or artifacts. It is also probable that they may be typicals that have been obliterated by noise/baseline wander or sudden posture changes. At this stage, the M, H, L tags are preliminary and primarily used to facilitate the identification process by applying rules based on contextual information. The M tag is very important in this analysis. If something matches a typical model, which is designed to track incoming QRS wave, there is very high probability that it is a QRS complex. However, that is not important at this stage whether there was an M in the other channel. Thus, seeing an M in a sequence of peak-pairs provides a high level of confidence to select it and start applying other contextual rules around it. It must be noted that this peak-pair containing an M may be rejected at a later stage, if necessary.

Next, the refractory period of the heart is employed to reject artifacts and identify QRS complexes. Refractory period is the time after a QRS complex, during which the heart muscle cannot respond to another stimuli to depolarize the heart, i.e., it cannot produce a QRS complex during this time. This physiologic phenomena is used to get rid of some obvious artifacts like P waves and T waves for typical beats.

All peak pairs before the terminating peak pair and within a refractory distance from it are excluded from further analysis. Similarly all peak pairs afer the last classified beat and within refractory distance from it are also excluded from further analysis. Any remaining intermediate peaks are further grouped into various groups which are at least a refractory distance apart.

Each group may include one or more peak-pairs, or there may be no groups at all. Next, an estimate is made of how many intermediate peaks can be accomodated between the last classified beat and the teminating peak pair. This estimate is made on the basis of distance between these beats, refractory period, and average heart rate at this point in time. This estimate is used as a guide in rejecting artifacts or looking for missing QRS complexes due to small amplitude.

One or more or all peak-pairs in a group can be artifacts. This is determined by examining individual peak pairs in each group and selecting the best peak pairs on following criteria:

a. Peak pair combination;
b. quality of the beat in both channels;
c. size of the beat in both channel;
d. degree of similarity with typical beat;
e. distance from neighboring beat;
f. alignment of peaks.

In this process, the best candidate is also picked up from each group. Also, two estimates of numbers of peak-pairs that can be selected from each group is made. One estimate is a minimal and the other one is the maximal estimate. These estimates from each group are combined and compared with the overall estimate obtained using the distance between the last classified beat and the terminating peak pair.

If the group estimate dictates a need to select more beats, further artifact rejection technique is applied. This is achieved by using some of the extracted features and the template matching techniques. Peak-pairs seen before as typical or atypical are selected in preferrence to new peak-pairs. This sort of approach makes the system intelligent, adaptive and learning.

If a peak-pair matches a typical beat template, this process is reiterated using it as the terminating peak pair. Using this kind of iteractive technique allows the system to make prudent decision starting out with small amounts of reliable information. Peak Sequences Containinq No M's:

Since there is no solid reliable information available in this case, the attempt is to make only one peak-pair selection to continue the process or translate this case to the previous case using the template matching technique. To achieve this, grouping of peak-pairs is performed as described in the previous case and best candidates identified in each group. Moreover, the peak pair that is closest to the typical beat is also selected from all the peak-pair sequences. Next, this pair is compared with typical beat templates using template matching technique. If it matches, then we have found an M, and this peak sequence can now be processed using more precise and powerful logic described before. This situation is not uncommon, because due to noise/baseline wander or posture changes, peaks may not be classified as an M. However, they made be picked up as M's using the template matching technique. This is an example of how two different techniques can be used to complement each other towards a common goal.

If no match is found with typical beat templates, the logic selects the best peak pair from the first group to continue the processing.

No Peak-Pairs Or Not Sufficient Peak-Pairs Found:

In either case, there is a probability that we missed some peak-pairs due to too high scanning threshold in both channels or the QRS complexes are small in both channels. It is also probable that there is nothing we missed. In any event, appropriate regions of ECG in both channels are scanned at low scanning threshold. If any peak-pairs are obtained during this scan, they are processes as described before. If nothing is picked up, further checks are made for some signal quality evaluation in each channel. If signal quality is not acceptable in the intermediate regions, proper shut-down information is generated and supplied for succeeding stages. If the signal is acceptable, this condition is accepted and the analysis proceeds further.

QRS Classification:

After identifying peak-pairs as QRS complexes, the next step is to classify them as typical/atypical. It must be noted that a preliminary classification has already been performed by the peak classification logic in the form of tagging peaks as M, H, L, S or A. However, this tagging may be incorrect. Even when correct, it may be conflicting in two channels, e.g., [M, H] or [M, L] combination indicates one channel is typical and other is atypical. In practice, it is not uncommon to see one channel showing large variation in typical shape due to posture changes or obliteration due to noise/baseline wander. In such cases, it is desirable to classify such combinations as typical. On the other hand, it is also not uncommon to see ventricular beats mimicking typical beat in one channel and being quite distinct from the typical beat in the other channel. In these instances, it is desirable to classify these combinations as atypical. Both cases mentioned above make two channel analysis very powerful and accurate compared to the single channel system which does not have this conflict to resolve and is more than likely to make improper classification!

To accomplish the task of classifying beat pairs properly, all the information available at this stage is used. This includes feature extraction information, contextual information, noise/baseline wander information, information on previous beats, emerging trends in the ECG, correlation with previously seen shapes etc.

To achieve this end, available information is used in a hierarchical decision making process. In this process, certain important information is proceessed first and if it is found to be reliable enough to make a final decision at this point, a decision is made. If not reliable enough, a next piece of information is examined and its reliability evaluated as described before. This process is iterated until a final decision is made. As can be seen that this approach tends to use all reliable information only when nothing more reliable is available. Deeper into the hierarchial process, information tends to be less reliable.

To start off the process, the beat pair is compared using correlation technique with typical and atypical templates seen so far. If the earlier stages have identified the beat pair as [M, M] it is always declares as typical. If not [M, M], it is compared with typical and atypical templates is evaluated. If there is a compelling evidence of a very good match with either type of templates, the beat pair is classified according to the template matching results. In case both types of templates show a good match, the tie is broken using contextual information like prematurity, neighboring beats, relative superiority of one match over the other etc.

In case of no very good matches, the feature extraction information and comparison information with the typical model is evaluated. Differences with the typical model are evaluated and depending upon the reliability of information, a decision may be made at this stage or not. If no decision is yet made, the beat pair is compared with neighboring known beat pairs, if available. This allows to adapt to changes in ECG due to posture changes. Sometimes, the adaptive logic to migrate the model is not fast enough to pick up some of these changes. This technique allows us to handle such situations properly.

Template generation and matching module classifies QRS complexes into various families or groups of similar beats on the basis of their shape. This is necessary to separate atypical beats from typical beats. After separating atypical beats, it is also necessary to further separate them into different groups on the basis of their shape. This is required to detect multiform ventricular activity in the ECG. It also allows the sytem to maintain separate statistics on each family during the procedure.

This module uses the correlation technique to separate beats into various families. The QRS complex under consideration is compared, sample for sample, with the representative of a family. Absolute differences from this sample for sample comparison are weighted and added up to determine the overall correlation value. This value is further normalized to handle QRS complexes of different sizes. This normalized correlation value is used as a measure of similarity between the beat and the family. The smaller the number, the better the correlation. Such correlation values are computed against appropriate existing families. If a family with low enough correlation value is found, a match is considered to have been found. If none found, then a decision to create a new family rests with the control logic. If no more families can be created, two closest existing families will be merged to make room for the new family. During this entire process, information is combined from both channels to make the final match or no match decision.

If the template level does not yield any results, at the next level, noise/baseline wander information and trends in noise/baseline information are used to shut down one or more channel, if appropriate. This late action on noise/baseline wander allows the system to apply global information to detect observations missed by localized processing performed at earlier stages.

Next, both template matching and feature extraction information is combined with the contextual information.

If all these and similar rules do not yield a decision, the beat-pair is classified as atypical and a new template created for it.

Another important function performed by this logic is establishing a new typical template when sudden shape changes throw it out of synchrony with incoming typical beats. This is achieved by recognizing the fact that one channel with the most of the time be tracking properly while the other channel may have lost the model due to sudden changes. In such cases when the beat pair is classified as typical, system recognizes the trend in the other channel of being consistently incorrect over a period of time. This signals it to reestablish the typical template based on new information. This is an excellent example of two channel correlation aiding in accurate analysis. Once the new typical template is established, the second channel will be able to contribute reliable information. A single channel system may never pick up this trend and may misclassify everything from this point onwards.

Another monitoring function performed by this logic is monitoring the signal amplitude in each channel. If there is a trend towards small amplitude, the channel is put in a low amplitude state. This piece of information is used by the rest of the system to deemphasize very small signals. Conversely, it also will observe the change back to good amplitude and get the channel out of the low amplitude state.

Event Classifier:

After identifying a QRS complex and identifying it as typical or atypical, all the information about it is passed on to the event classifier module. The function of this module is to detect and identify various cardiac events associated with a QRS complex or a set of QRS complexes. Based upon the amount of contextual information used in detecting, these events are divided into three major steps:

A. Single Beat Events: As the name implies, these events are detected using the information associated with a single QRS complex. These events are primarily based upon classifying a QRS complex as on-time, premature, or late. This timing classification is coupled with the typical/atypical classification to produce familiar cardiac event like SPBs, VPBs, Fusion Beats, Escape Beats, Missed Beats, etc.

B. Multiple Beat Events: As the same implies, these events are detected using a sequence of beats or QRS complexes. Those events are primarily based upon detecting and identifying various clinically significant typical an atypical beat sequences, e.g., a couplet consists of two consecutive atypical beats; a triplet consists of three consecutive atypical beats; a ventricular tachycardia consists of four or more consecutive atypical beats; a bigeminy consists of alternating typical and atypical beats etc. Some multiple beat events are of fixed length in terms of number of beats they comprise of, e.g., a couplet consists of two beats. On the other hand, other multiple beat events have variable length, e.g., a bigeminy may consist of a different numbers of alternating pairs of typical and atypical beats. Onset and offset for each multiple beat event are identified by this module.

C. Rate Events: These events are detected using the rate information associated with QRS complexes. Average heart rate is computed using the last eight beats. This average rate is used to determine the rate event classification. In some instances, rates are also used to detect and classify sustained or non-sustained tachycardia. Four beat average rate is also used in determining sudden rate increases and sudden rate decreases.

As explained above, each QRS complex may be assigned up to three different event classifications. These classifications are combined to produce the final event classification preserved in the report. However, individual event classifications are also used for statistical summarization.

Statistical Collector:

Once a QRS complex is detected, identified, and one or more events associated with it, this information is supplied to the statistical collector module. The function of this module is to collect various statistics required in the report. These include:

a. hourly counts for all Events;
b. R-R interval distribution;
c. Min/avg/max heart rate, number of SVPB's and number of VPB's for each summary period (normally ten minutes) of the procedure;
d. number of different QRS families and number of members in each of them;
e. for each atypical family, hourly summary for various events started by this family;
f. amount of time each channel was shut down due to inadequate signal;
g. log of major cardiac events detected.

ECG Strip Manager:

After the event classifier has classified events and statistical collector has summarized the necessary information, the information is supplied to the ECG strip Manager. The function of this module is to select and save sample ECG strips for later documentation in the report of various cardiac events detected during the procedure. The objective here is to produce a very comprehensive report that is indicative of the kind of cardiac activity seen during the procedure.

Since the amount of memory that is available for storing sample ECG strips is limited, it is not possible to save a ECG strip for every occurrence of each event. However, it is not necessary to save every occurrence of each event. What is necessary is a collection of strips that represent the cardiac activity seen. This mandates very careful management of the available memory.

Various events are classified into three major groups, i.e., ventricular, superventricular and bradycardiac. Each group is allocated a certain precentage (quota) of the available memory for ECG strips. Events belonging to each group can only use the quota assigned to them to save their ECG strips. This quota scheme enables the user to control and emphasize the groups in the report. Any unused memory belonging to a group can be used by other groups, if required. However, this memory unit must be returned to the original group, if it needs at a later point. This strategy enables memory quotas to be maintained when there is contention, otherwise, allows free usage of available memory. This prevents any memory from being wasted.

Within each group, events are ordered according to their significance from a clinical standpoint. This priority ordering can be modified by the user during the initialization of the procedure. This priority ordering is used to determine which events are more important than other. So, if there is memory contention and all quotas are filled up, higher priority events will be saved in favor of the lower priority events. However, to prevent a single higher priority event from taking up a group's quota entirely or a large chunk of it, priority of each event is reduced as an ECG strip is taken for it. As a result, a previously low priority event may now appear as a high priority event. This concept of dynamic priority allows the system to produce a comprehensive set of ECG strips in each group.

If all the quotas are running full and the priority of an event has reached the lowest point and a new occurrence of the event is detected. At this point, the ECG strip for the new occurrence cannot be taken at the expense of other events. However, it is possible to replace the existing sample of the event, if the new sample is a better example of the event. This also solves the problem of filling up of quotas during the early stages of the procedure, provided there is enough activity, and then not taking no new sample ECG strip. Under the quality factor oriented replacement scheme, better examples occurring at a later point will be saved instead of the earlier samples.

Quality factors for different events are different, e.g., tachycardia events require that higher rate events be saved, while bradycardia events require that lower rate events be saved. Various different quality factors are employed for different events. Some of the factors used are: amount of prematurity, lateness, noise, baseline wander, occurrence of a new form, average rate, sudden rate shifts, time of occurrence etc.

In order to make a more efficient usage of available memory, the length of ECG strip for different events is not the same. Instead, different length strips are taken for different events. Five different strip lengths, for example, 4, 6, 7.6, 12, and 14 seconds, are used. Events requiring only small amounts of contextual information use smaller strip lengths. On the other hand, longer strip lengths are used to document events requiring more contextual information. In resolving storage conflicts, more than one event of another class or type may have to be detected to accomodate a larger event type.

ECG Strip Compression:

In order to make an efficient usage of the available memory in saving the maximum of information, ECG data for a strip is compressed before storing it. The compression scheme involves saving signal extrema and then compressing first differences in variable length bit fields. This concept is based on the observation that most of the time ECG does not change rapidly from one sample point to the other. Consequently, the first differences between successive ECG signal values can be represented by much smaller numbers than the original ECG signal value. Moveover, knowing the starting ECG signal value, the entire ECG signal can be reconstructed using the first differences. To save these first differences, different numbers of bits are used depending upon the value of the first difference. Smaller numbers are represented using the fewest bits and larger ones, are represented using larger numbers of bits. This compression scheme results, on average, in a 4:1 data compression of a 250 Hz ECG signal. This compressed data is decompressed by the OMEGA base station before printing the report.

ELECTRONIC DIARY

Figure 15:
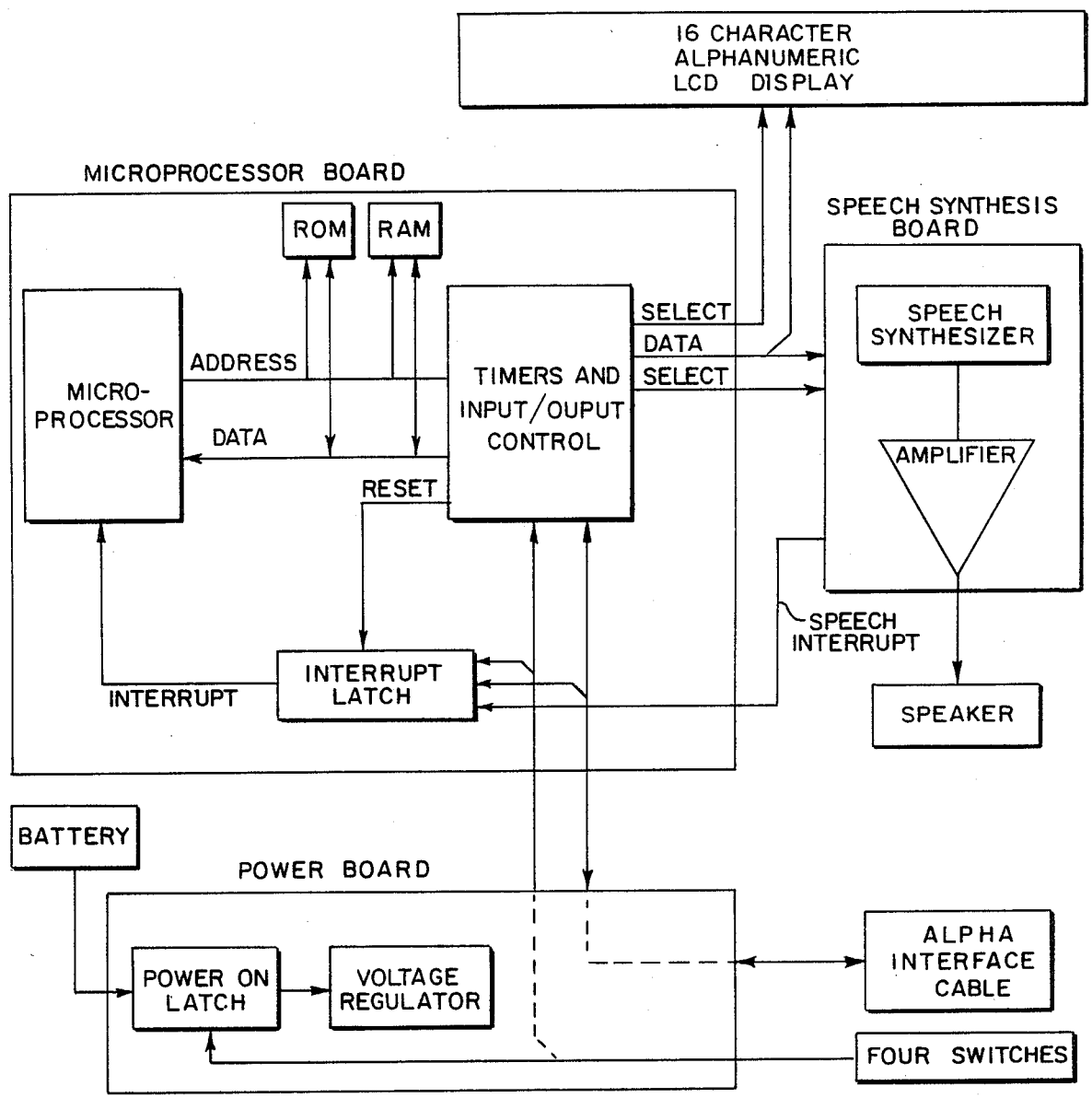
FIG. 15 is a block diagram of the electronic diary.

The Electronic Diary 60, as illustrated in FIG. 15, is comprised of three circuit boards, a 16-character alphanumeric LCD Display Module, four switches, and a speaker. It is powered by a single 9-volt battery and attaches to the Alpha Computer via a coiled cable.

The first board is the power board and contains a power on latch, voltage regulator, and associated support logic for the system. The connections required for this board are the battery, four switches, Alpha interface cable, and ribbon cable to the processor board. Once the battery is connected, no power is applied to the system until the power-on latch is activated by pressing the on/off switch. The battery is then connected to the voltage regulator and power is applied to the system.

The second board in the system is the microprocessor board. It is comprised of an eight bit microprocessor, Read Only Memory (ROM), Random Access Memory (RAM), a peripheral controller, interrupt latch, and associated support logic. The ROM contains the program that communicates with the Alpha computer to load the main program and speech text. The RAM is used to store the main program and speech text downloaded from the Alpha. A peripheral controller contains the timers and necessary logic to provide control and data information to the LCD display and rest of the system. The interrupt latch is used to interrupt the processor when specific events occur in the system.

The third board is the speech synthesis board. This board contains the speech synthesizer and amplifier necessary to drive the internal speaker.

The Diary, in operation, is activated by either the Alpha computer or by pressing the on/off switch. Either will generate an interrupt which will bring the system out of power save mode and active the main program. Data is sent to the LCD display to present the appropriate message and a byte of speech data if sent to the speech synthesis board. Upon receiving the byte of speech data, the speech synthesis comes out of its own power save mode and beings processing the speech data. The amplifier is turned on and speech output begins. After each byte or speech data is processed, an interrupt is sent to the processor to indicate that it is ready for another byte. This continues until the processor has completed the desired message. Patient responses to the questions presented are entered via the four switches which in turn generate their own interrupt. Once the session is complete, the processor places the system back in power save mode to prolong battery life.

From the preceding description of the preferred embodiments, it is evident that the objects of the invention are attained, and although the invention has been described and illustrated in detail, it is to be clearly understood that the same is by way of illustration and example only and is not to be taken by way of limitation. The spirit and scope of the invention are to be limited only by the terms of the appended claims.

What is claimed is:

1. A cardiac analyzer comprising:
   first and second input means for receiving input signals from separate sources;
   means for detecting peaks in the input signals of both input means;
   means for classifying detected peaks for both input means;
   means for providing classification pairs, one from each input means at a corresponding time;
   means for analyzing said detected peak pairs and said peak pair classification; and
   means for identifying which peaks are QRS complexes.

2. A cardiac analyzer according to claim 1 including means for controlling said peak detecting means and classifying means to detect and classify a peak from the input signals from said first input means and then peak detect and classify input signals in said second input means at the corresponding time as said detected peak in said first input means.

3. A cardiac analyzer according to claim 2 including threshold means for detecting peaks above a threshold and means for switching said threshold of said threshold means from a high to a low threshold for detecting peaks when a peak is not found in said second channel at said corresponding time at said high threshold.

4. A cardiac analyzer according to claim 3 wherein said classsifying means includes means for classifying a peak detected at a low threshold as low.

5. A cardiac analyzer according to claim 3 including means for monitoring said QRS complexes and adjusting said high threshold value as a function of said monitoring.

6. A cardiac analyzer according to claim 1 wherein said peak classifying means includes means for comparing said detected peaks with a model QRS wave, and providing a matched and non-matched peak classification between said detected peak and said model QRS wave.

7. A cardiac analyzer according to claim 6 wherein said peak classifying means includes means for detecting noise in said input signals, means for detecting baseline shift in said input signals, and means for classifying an input signal as unacceptable as a function of detected noise and baseline shift.

8. A cardiac analyzer according to claim 7 including means for activating said noise and baseline shift detecting means when a non-matched peak classification is present.

9. A cardiac analyzer according to claim 8 including means for shutting down an input means for deleting noise or baseline shifted signal.

10. A cardiac analyzer according to claim 7 including means for activating said noise and baseline shift detecting means when a matched peak classification is not present in both input means at the same time.

11. A cardiac analyzer according to claim 6 including buffer means for holding a sliding window of input signals and means for storing of a portion of said window of input signals substantially centered on the event to be stored in response to a matched peak classification.

12. A cardiac analyzer according to claim 11 including means for controlling said peak detecting means and peak classifying means to detect and classify input signals in said second input means at time adjacent said corresponding time of and until a matched peak classification is achieved and subsequently detect and classify peaks in said first output means at the corresponding time as the detected match classified peak in said second input means.

13. A cardiac analyzer according to claim 6 including means for determining input signals at said input means below a given value for non-matched peak classification and said classifying means includes means for classifying said determined below input signals unacceptable until said comparing means indicates a match with said model.

14. A cardiac analyzer according to claim 6 including means for extracting features of said detected peaks, and means for comparing extracted features of said detected peaks with features of said model QRS wave.

15. A cardiac analyzer according to claim 14 including means for adjusting said features of said model QRS wave for matched peak classification.

16. A cardiac analyzer according to claim 1 including means for classifying identified QRS compelxes as typical or atypical.

17. A cardiac analyzer according to claim 16 including means for comparing identified QRS complexes with a plurality of typical and atypical QRS templates and said QRS classifying means include means for classifying said QRS complex based on said template comparison and peak pair classification.

18. A cardiac analyzer according to claim 16 including means for extracting features of said detected peaks, and means for comparing extracted features of said detected peaks with features of a model QRS wave; and wherein said peak classifying means include means for classifying a match of features from said feature comparing means, and said QRS classifying means includes means for classifying based on said extracted features.

19. A cardiac analyzer according to claim 16 including means for determining an acceptable level of said input signals; and wherein said peak classifying means includes means for classifying peaks based on input signal acceptability, said QRS identifying means includes means for identifying QRS complexes based also on input signal acceptability, and said QRS classifying means includes means for classifying QRS complexes based also on input signal acceptability.

20. A cardiac analyzer according to claim 1 including threshold means for detecting peaks above a threshold; and wherein said peak classifying means and QRS identifying means include control means for switching the threshold state of said threshold means from a high to a low threshold as a function of peak classification and QRS identification and means for classifying peaks and identifying QRS complexes as a function of the threshold state.

* * * * *